United States Patent [19]

Theeuwes et al.

[11] 4,077,407
[45] Mar. 7, 1978

[54] OSMOTIC DEVICES HAVING COMPOSITE WALLS

[75] Inventors: Felix Theeuwes, Los Altos; Atul D. Ayer, Belmont, both of Calif.

[73] Assignee: Alza Corporation, Palo Alto, Calif.

[21] Appl. No.: 634,859

[22] Filed: Nov. 24, 1975

[51] Int. Cl.² ............................................. A61M 31/00
[52] U.S. Cl. ..................................... 128/260; 106/196; 128/213; 210/500 M; 264/49; 424/19; 424/20
[58] Field of Search ................... 128/260, 213; 424/19, 424/20; 106/196; 210/500 M; 264/49

[56] References Cited

U.S. PATENT DOCUMENTS

| 3,129,159 | 4/1964 | Maier et al. | 160/196 |
|---|---|---|---|
| 3,460,683 | 8/1969 | Cannon | 106/196 |
| 3,497,072 | 2/1970 | Cannon | 106/196 |
| 3,522,335 | 7/1970 | Rowley | 106/196 |
| 3,567,809 | 3/1971 | Wataru et al. | 106/196 |
| 3,567,809 | 3/1971 | Ueno et al. | 210/500 M |
| 3,592,671 | 7/1971 | Malm et al. | 106/196 |
| 3,592,672 | 7/1971 | Rowley et al. | 106/196 |
| 3,607,329 | 9/1971 | Manjikian | 210/500 M |
| 3,646,179 | 2/1972 | Stana | 106/196 |
| 3,721,623 | 3/1973 | Stana | 210/500 M |
| 3,760,806 | 9/1973 | Leeper | 128/260 |
| 3,772,072 | 11/1973 | Brown et al. | 210/500 M |
| 3,780,147 | 12/1973 | Stana | 106/196 |
| 3,807,571 | 4/1973 | Walmsley | 106/196 |
| 3,845,770 | 11/1974 | Theeuwes et al. | 128/260 |
| 3,863,633 | 2/1975 | Ryde et al. | 128/260 |
| 3,875,300 | 4/1975 | Homm et al | 128/260 |
| 3,878,276 | 4/1975 | Hoernschemeyer | 210/500 M |
| 3,916,899 | 11/1975 | Theeuwes et al. | 128/260 |
| 3,929,132 | 12/1975 | Higuchi | 128/260 |
| 3,938,515 | 2/1976 | Leeper et al. | 128/260 |

Primary Examiner—Stephen C. Pellegrino
Assistant Examiner—Teddy S. Gron
Attorney, Agent, or Firm—Paul L. Sabatine; Thomas E. Ciotti; Edward L. Mandell

[57] ABSTRACT

An osmotic device for delivering an active agent is disclosed. The device is comprised of a wall surrounding a compartment and has a passageway through the wall for releasing the agent. The wall is formed of a multiplicity of materials comprising a material permeable to an external fluid and substantially impermeable to agent and at least one additional material selected from a material that imparts stability to the wall, enhances the permeability of the wall to fluids, or aids in forming the wall. The compartment comprises an active agent that exhibits an osmotic pressure gradient against an external fluid, or the agent is mixed with an osmotically effective compound that exhibits an osmotic pressure gradient against the fluid. Agent is released from the device by fluid being imbibed through the wall into the compartment at a rate controlled by the permeability of the wall and the osmotic pressure gradient across the wall, to produce a solution containing agent that is released through the passageway at a controlled and continuous rate over a prolonged period of time.

11 Claims, 14 Drawing Figures

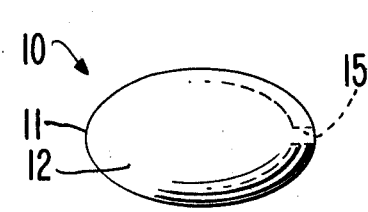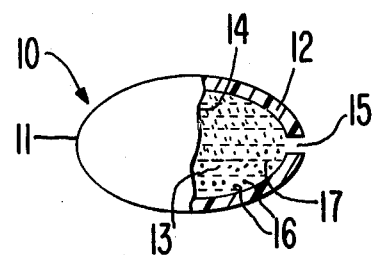
FIG. 1A  FIG. 1B
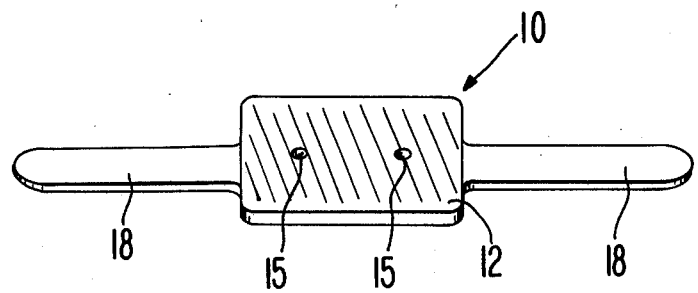
FIG. 2
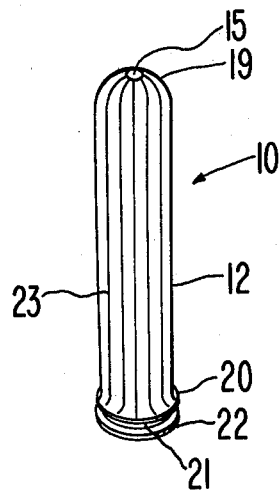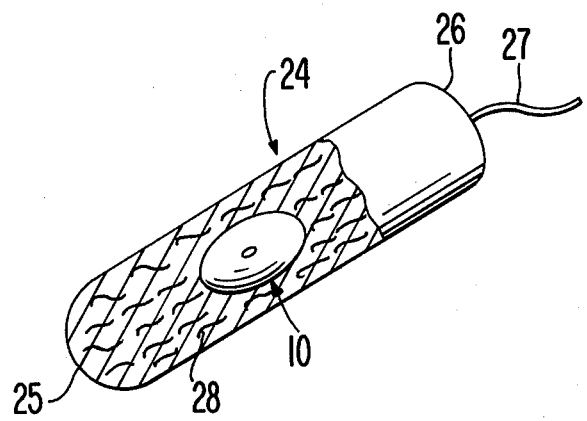
FIG. 3  FIG. 4

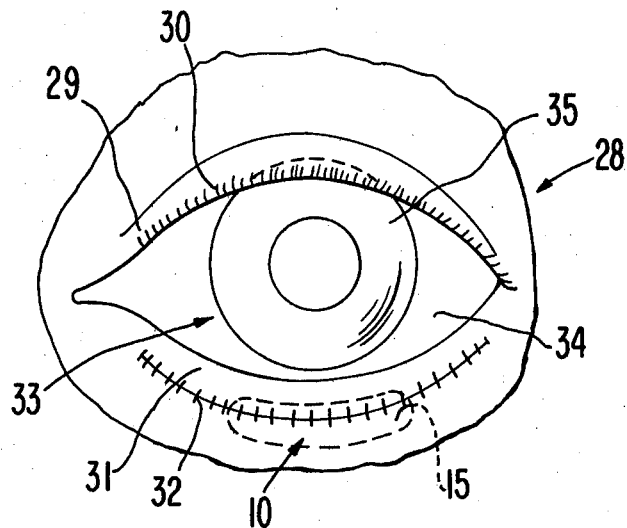
FIG. 5
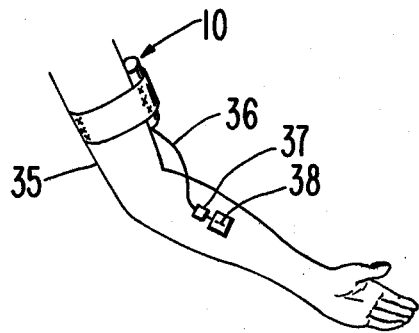
FIG. 6
FIG. 7
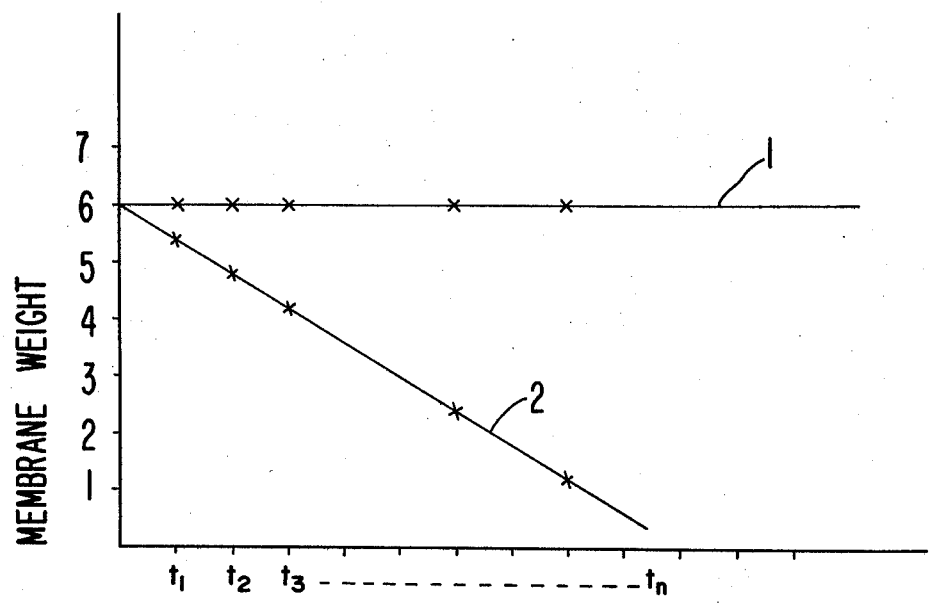

OSMOTIC DEVICES HAVING COMPOSITE WALLS

FIELD OF THE INVENTION

This invention pertains to an osmotic device. More particularly, the invention relates to an osmotic device having a wall formed of a plurality of semipermeable wall forming materials for delivering an active agent at a controlled and continuous rate over a prolonged period of time to an environment of use.

BACKGROUND OF THE INVENTION

Osmotic devices for delivering a beneficial agent to an environment of use are known to the prior art in U.S. Pat. Nos. 3,845,770 and 3,916,899. The devices disclosed in these patents are made with a wall formed of a material that is permeable to an external fluid and substantially impermeable to agent. The wall surrounds a compartment that contains an agent and there is a passageway through the wall for dispensing the agent. These devices are remarkably effective for delivering an agent that is soluble in the fluid and exhibits an osmotic pressure gradient across the wall against the fluid, and for delivering an agent that has limited solubility in the fluid and is admixed with an osmotically effective compound soluble in the fluid that exhibits an osmotic pressure gradient across the wall against the fluid. The devices release agent by fluid being continuously imbibed through the wall into the compartment at a rate determined by the permeability of the wall and the osmotic pressure gradient across the wall to produce a solution of soluble agent, or a solution of soluble compound containing agent which solution in either operation is dispensed from the device. While the above devices represent a significant and pioneer advancement in the art and they are useful for dispensing numerous agents, there is an occasional instance where the agent may have an unwanted effect on the device. For example, a wall formed of cellulose acetate having a low acetyl content in the presence of certain agents can slowly loose its integrity over a prolonged period of time thereby slowly changing the rate of imbibition and concomitantly the rate of agent release from the device over a correspondingly prolonged period of time.

OBJECTS OF THE INVENTION

Accordingly, it is an immediate object of this invention to provide an improved osmotic device for the controlled and continuous dispensing of an active agent over a prolonged period of time which device overcomes the problems known to the prior art.

Another object of the invention is to provide an osmotic device that maintains its physical and chemical integrity during the controlled and continuous dispensing of an agent over a prolonged period of time.

Yet another object of the invention is to provide an osmotic device designed with a minimum number of parts and having at least one wall formed of a plurality of wall forming materials that makes the wall substantially inert towards agents and solutions thereof.

Another object of the invention is to provide an osmotic device for dispensing drugs that because of their inherent properties are difficult to dispense, and which drugs can be dispensed with the device of this invention at a controlled and continuous rate to perform their intended therapeutic effects.

Still a further object of the invention is to provide an osmotic dispensing system that can administer a complete pharmaceutical regimen to a human for a particular time period, the use of which requires intervention only for initiation and possibly termination of the regimen.

Still a further object of the invention is to provide osmotic devices having a wide spectrum of semipermeable walls in which wall properties such as the fluid flow-through rate and agent resistance may be controlled and varied to the particular application.

Still another object of the invention is to provide an improved osmotic device for delivering drugs that are difficult to deliver and drugs that require multiple doses, and which device can deliver the drugs over a prolonged period of time and also eliminate the necessity for taking multiple doses of drug.

Yet still another object of the invention is to provide an osmotic device having a wall that has a high flux rate to fluids, a high degree of exclusion towards agents and improved resistance to hydrolysis in the presence of agents over a wide pH range.

Yet still another object is to provide an osmotic device that can deliver all kinds of drugs and has an economic advantage for the user by keeping to a minimum the number of doses to be administered and reducing missed doses because of forgetfulness.

Other objects, features and advantages of the invention will be more apparent to those skilled in the art from the following specification, taken in conjunction with the drawings and the accompanying claims.

SUMMARY OF THE INVENTION

This invention concerns an osmotic device useful for dispensing an active agent to an environment of use. The device is comprised of a wall surrounding a compartment and has a passageway communicating with the compartment and the exterior of the device. The compartment contains either an agent that exhibits an osmotic pressure gradient across the wall against an external fluid, or it contains a mixture of an agent and an osmotically effective compound that exhibits an osmotic pressure gradient across the wall against the fluid. The wall is comprised of a blend of a wall forming material with the wall being permeable to the external fluid, substantially impermeable to agent and substantially inert to agent and solutions thereof. Agent is dispensed from the device by fluid being imbibed through the wall into the compartment to dissolve agent or the compound and produce a solution that is released under osmotic pressure from the device through the passageway at a controlled and continuous rate over a prolonged period of time.

BRIEF DESCRIPTION OF THE DRAWINGS

In the drawings, which are not drawn to scale, but are set forth to illustrate various embodiments of the invention, the figures are as follows:

FIG. 1A is a view of an osmotic device designed for orally delivering a beneficial agent.

FIG. 1B is a view of the device of FIG. 1A in opened-section for illustrating the structure of the wall and the compartment of the device.

FIG. 2 is a view of an osmotic device manufactured for topically administering drug.

FIG. 3 is a perspective view of another embodiment of the invention comprising a device shaped as an anal, osmotic drug delivery device.

FIG. 4 shows an osmotic device designed for releasing drug in the vaginal cavity.

FIG. 5 is a front view of the human eye illustrating an osmotic device in operative position in the environment of use.

FIG. 6 is a view diagrammatically illustrating an osmotic device delivering drug to a drug receptor site.

FIG. 7 is a graph comparing a material that is inert with a material that slowly loses its integrity in the presence of agent.

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 8:
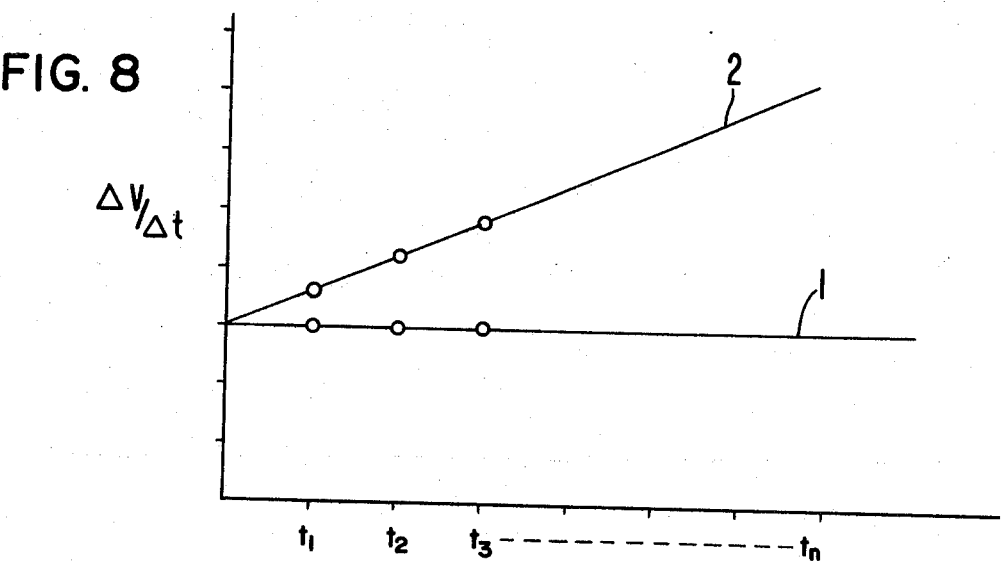
FIG. 8 is a graph comparing the fluid flux through a wall that maintains its integrity in the presence of fluid with a wall that slowly loses its integrity in the presence of fluid.

Turning now to the drawings in detail, which are examples of various osmotic delivery devices of the invention, and which examples are not to be considered as limiting, one example of an osmotic device is indicated in FIGS. 1A and 1B, considered together, by numeral 10. Device 10 is comprised of a body 11 having a wall 12 that surrounds a compartment 13, seen in FIG. 1B in opened-section with a portion of wall 12 removed at 14, and a passageway 15 in wall 12 that communicates with compartment 13 and the exterior of device 10. Compartment 13, as seen in FIG. 1B, in one embodiment is a means for containing an agent 16 that is soluble in an external fluid and exhibits an osmotic pressure gradient across wall 12 against the fluid, or compartment 13 can contain a mixture of agents with at least one agent exhibiting an osmotic pressure gradient. In another embodiment, compartment 13 contains an agent that has limited solubility or is substantially insoluble in the external fluid mixed with an osmotically effective compound 17 that is soluble in the external fluid and exhibits an osmotic pressure gradient across wall 12 against the fluid. Compartment 13 also can contain other compounds 17 such as a surfactant for wetting the agent and a non-toxic dye for either identifying the agent or for making release of agent visible to the eye.

Wall 12 of device 10 is comprised in whole or in at least a part of a composite of at least two wall forming materials blended to form a wall that is, a) permeable to the passage of an external fluid, b) substantially impermeable to the passage of agent 16 and other compounds 17 housed in compartment 13, c) is substantially inert in the presence of agent 16, compound 17 and solutions thereof, and d) maintains its physical and chemical integrity in the environment of use during the dispensing of active agent. When wall 12 is formed in part of a semipermeable composite, the remainder of 12 is formed of a material that is substantially impermeable to fluid and to the passage of agent 16 and compound 17 housed in compartment 13. A detailed description of wall forming materials, agents and other compounds appears later in the specification.

In operation in the environment of use, device 10 in one embodiment releases agent 16 housed in compartment 13 and soluble in the external fluid by fluid being imbibed into compartment 13 in a tendency towards osmotic equilibrium at a rate controlled by the permeability of wall 12 and the osmotic pressure gradient across wall 12 to continuously dissolve agent 16 which is osmotically pumped from device 10 through passageway 15 at a controlled and continuous rate over a prolonged period of time. Device 10, in another embodiment, releases agent 16 that has limited solubility in the fluid and is mixed with an osmotically effective compound 17 by fluid being imbibed through wall 12 into compartment 13 in a tendency towards osmotic equilibrium at a rate controlled by the permeability of wall 12 an the osmotic gradient across wall 12 to continuously dissolve compound 17 to form a solution containing agent 16 which is pumped from device 10 through passageway 15 at a controlled and continuous rate over a prolonged period of time.

Device 10 of FIGS. 1A and 1B can be made in many embodiments including the presently preferred embodiment for oral use, that is, for releasing in the gastrointestinal tract either a locally or systematically acting therapeutic agent over a prolonged period of time. Oral device 10 can have various conventional shapes and sizes such as round with a diameter of 3/16 inch to ½ inch, or it can be shaped like a capsule having a range of sizes from triple zero to zero, and from 1 to 8.

FIG. 2 represents another device 10 manufactured according to the invention and designed for topically administering drug. Device 10 is comprised of a semipermeable composite wall 12 surrounding a compartment, not shown, that contains an agent or a mixture of agent and an osmotically effective compound. Device 10 has two passageways for releasing drug. Passageways 15 can be of the same or of different sizes so long as the total opened area lets device 10 operate as an osmotic device. Device 10 has a pair of integral straps optionally either coated with an adhesive for suitably mounting device 10 to the surface of an animal, not shown, or straps 18 can have fastening strips of the Velcro ®-type as disclosed in U.S. Pat. No. 3,086,529 on their ends for fastening device 10 around an arm or leg for administering drug thereto. It is sometimes preferred to fix one-half of each of the Velcro ® strips on device 10 to mate with the opposite strip on strap 18. Device 10 operates to release drug topically in the same way device 10 of FIGS. 1A and 1B operate to release agent 16 to the environment of use.

FIG. 3 illustrates an osmotic device 10 designed for releasing an agent within a body opening, the anal canal not shown. Device 10 is shaped like a tube and it has a lead end 19, a distant trailing end 22 and a plurality of circumferentially spaced ribs 23 extended along the length of device 10. Ribs 23 at end 22 unite with a downwardly facing shoulder 20 that is formed with an annular removable closure 21 for filling device 10. Ribs 23 serve to grasp the cellular wall of the anal canal and also to increase the exposed surface of device 10 for imbibing anal fluid into the device. Wall 12 of device 10 is comprised of a semipermeable composite material and it surrounds a compartment, not shown, that contains an agent. A passageway 15 at end 19 extends through wall 12 for releasing agent from the compartment to the exterior of device 10. Device 10 of FIG. 3 releases either a locally or systemically acting agent in the anal canal in the same way device 10 of FIGS. 1A and 1B release agent 16 to an environment of use.

FIG. 4 shows an osmotic device 10 within a vaginal tampon 24 that is designed for placement in a vagina. Tampon 24 has an elongated, cylindrical, precompressed, self-sustaining shape with a rounded lead end 25 and a slightly curved rear end 26. Tampon 24 is made of cotton wadding 28 and it is equipped with a manually controlled cord 27 for easily removing it from a vagina. Tampon 24 serves as a platform for osmotic device 10. Device 10 is structurally identical with device 10 as described above and it also operates in a like manner. Device 10 of FIG. 4 in one embodiment contains a drug designed for absorption by the vaginal mucosa to produce a local or systemic effect. In another embodiment, device 10 contains an odor reductant that emits an odor counteracting scent or fragrence in the vagina.

Referring to FIG. 5, device 10 is seen in an eye 28 for administering drug at an osmotically metered dosage rate. In FIG. 5, eye 28 is comprised of an upper eyelid 29 with eyelashes 30 and a lower eyelid 31 with eyelashes 32. Eye 28 anatomically is comprised of an eyeball 33 covered for the greater part by sclera 34 and at its center area 35. Cornea 35. Eyelids 29 and 31 are lined with an epithelial membrane or palpebral conjunctiva, and sclera 34 is lined with a bulbar conjunctiva that covers the exposed surfaces of eyeball 33. Cornea 35 is covered with a transparent epithelial membrane. The portion of the palpebral conjunctiva which lines upper eyelid 30 and the underlying portion of the bulbar conjunctiva defines an upper cul-de-sac, while that portion of the palpebral conjunctiva which lines lower eyelid 31 and the underlying portion of the bulbar conjunctiva defines a lower cul-de-sac. Ocular, osmotic device 10 is designed for placement in the upper or lower cul-de-sac. Device 10 is seen in the lower cul-de-sac and it is held in place by the natural pressure of lower eyelid 31. Device 10 contains an ophthalmic drug for osmotic release to eye 28.

Ocular device 10 can have any geometric shape that fits comfortably in the cul-de-sac. Typical shapes include ellipsoid, bean, banana, circular, rectangular, doughnut, crescent and half-ring shaped devices. In cross-section, the devices can be doubly convex, concavo-convex, rectangular and the like, as the device in use will tend to conform to the shape of the eye. The dimensions of an ocular device can vary widely with the lower limit governed by the amount of drug to be supplied to the eye as well as by the smallest sized device that can be placed into the eye. The upper limit on the size of the device is governed by the space limitation in the eye consistent with comfortable retention in the eye. Satisfactory devices generally have a length of 4 to 20 millimeters, a width of 1 to 15 millimeters. The ocular device can contain from 0.15 micrograms to 100 milligrams of drug, or more, and it is made from non-erodible and inert materials that are compatible with the eye and its environment.

FIG. 6 diagrammatically illustrates the use of osmotic device 10. In FIG. 6, there is seen device 10 mounted on the arm 35 of a human for administering drug thereto. Device 10 is connected through passageway 15, not shown, to one end of a flexible conduit 36 which is connected at its other end to a needle 37 for releasing drug to drug receptor 38. Device 10 is structured and operates as previously described and it administers drug at a controlled and continuous rate to receptor 38, the antecubital vein, not shown, for a prolonged period of time.

While FIGS. 1 through 6 are illustrative of various devices that can be made according to the invention, it is to be understood these devices are not to be construed as limiting, as the devices can take a wide variety of shapes, sizes and forms for delivering agent to different environments of use. For example, the devices include buccal, implant, artificial gland, cervical, intrauterine and ear devices. The devices also can be adapted for delivering an active agent in streams, aquariums, fields, factories, reservoirs, laboratory facilities, hot houses, transportation means, navel means, air and military means, hospitals, veterinary clinics, nursing homes, chemical reactions, and other environments of use.

DETAILED DESCRIPTION OF THE INVENTION

In accordance with the practice of the invention, it has now been found that device 10 can be manufactured with an improved wall(s) comprised of at least two wall forming materials blended to form a wall that is, a) permeable to the passage of an external fluid present in the environment of use, b) substantially impermeable to the passage of agent 16 and other compounds 17 housed in compartment 13, c) is substantially inert in the presence of agent 16, compounds 17 and solutions thereof, and d) maintains its physical and chemical integrity in the environment of use during the dispensing of agent 16. Wall 12 is comprised of, 1) at least one wall forming material permeable to the fluid and substantially impermeable to agent 16 and other compounds 17 blended with at least one or more of the following wall forming materials, 2) a stabilizing material that imparts physical and chemical integrity to wall 12, and more particularly gives wall 12 inertness towards agent 16, compounds 17, solutions thereof, and to compounds present in the environment of use, 3) a flux enhancer that promotes the permeability of fluid through wall 12, 4) a plasticizer that gives flexibility to the wall, and 5) a dispersant useful for blending the materials into an operative integral composite wall. The wall's integrity or inertness to agents in the compartment, and to fluids and other compounds in the environment of use can, according to the mode and manner of the invention, be precisely regulated by selecting the ingredients blended into the wall forming the device. The fluid permeability of the wall can be regulated in a like manner. The term "composite" as used herein means the wall is comprised of a blend of materials that act together to form the operative integral wall of the device.

Exemplary materials for forming wall 12 that are permeable to fluids and impermeable to agents and impermeable to other compounds include membranes known to the art as osmosis and reverse osmosis membranes. These membranes, that are useful for the purpose identified above by 1), generically include wall forming polysaccharides comprised of anhydroglucose units. In one embodiment, the polysaccharides are cellulose esters having a degree of substitution, D.S., on the anhydroglucose unit from greater than 0 up to 3 inclusive. By "degree of substitution" as used herein is meant the average number of hydroxyl groups on the anhydroglucose unit replaced by a substituting group. Exemplary materials are represented by Formula 1:

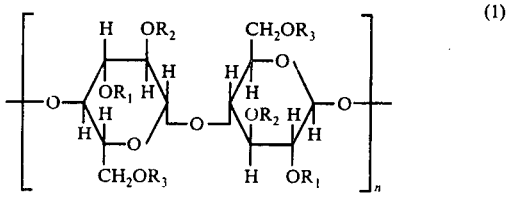

wherein $R_1$, $R_2$ and $R_3$ are the same or different and they are selected from the group consisting of hydrogen and acyl,

with at least one or all of $R_1$, $R_2$ and $R_3$ in the anhydroglucose unit either partially or completely substituted with the acyl moiety. The acyl moiety at $R_1$, $R_2$ and $R_3$ can be the same or different; and, $R_4$ is a member selected from the group consisting of hydrogen, alkyl groups of the straight or branched chain type having from 1 to 20 carbons and alkenyl groups that are straight or branched and have from 2 to 20 carbon atoms. Typical acyl moieties include alkanoyl and alkenoyl such as formyl, acetyl, propionyl, butyryl, hexanoyl, heptanoyl, octanoyl, undecanoyl, lauroyl, palmitoyl, stearoyl, oleoyl, and isomeric forms thereof; and $n$ in a presently preferred embodiment is a positive number greater than 5.

Representative materials embraced by Formula 1 include polymeric cellulose esters and copolymeric cellulose esters such as mono, di, and tricellulose acylates. Exemplary polymers include cellulose acetate having a D.S. up to 1 and an acetyl content of up to 21%; cellulose diacetate having a D.S. of 1 to 2 and an acetyl content of 21 to 35%; cellulose triacetate having a D.S. of 2 to 3 and an acetyl content of 35 to 44.8%; cellulose propionate having a D.S. of 1.8 and a propionyl content of 38.5%; cellulose acetate propionate having an acetyl content of 1.5 to 7% and a propionyl content of 39 to 42%; cellulose acetate propionate having an acetyl content of 2.5 to 3%, an average combined propionyl content of 39.2 to 45% and a hydroxyl content of 2.8 to 5.4%; cellulose acetate butyrate having a D S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution prepared by the hydrolysis of the corresponding triester to yield cellulose diacylates having a D.S. of 2.2 to 2.6 such as cellulose disuccinate, cellulose dipalmitate, cellulose dioctanoate, cellulose dicaprylate, and cellulose dipentanate; and esters prepared from acyl anhydrides or acyl acids in an esterification reaction to yield esters such as cellulose acetate valerate, cellulose acetate succinate, cellulose propionate succinate, cellulose acetate octanoate, cellulose valerate palmitate, cellulose acetate palmitate, and cellulose acetate heptanoate. Generally, the materials useful for forming the wall will have a fluid permeability of $10^{-5}$ to $10^{-1}$ (cc.mil/cm².hr.atm), expressed per atmosphere (atm) of hydrostatic or osmotic pressure difference across the membrane at the temperature of use while possessing a high degree of impermeability to solute are useful for the purpose of the invention. The polymers described above are known to the art or they can be prepared according to the procedures in *Encyclopedia of Polymer Science and Technology*, Vol. 3, pages 325 to 354, 1964, published by Interscience Publishers Inc., New York.

The materials forming wall 12 will, in a presently preferred embodiment, include at least one material embraced by Formula 1. Wall 12 also can include a wall forming stabilizing material identified above as 2). This latter material is a different material than the wall forming material and it is either selected from the materials embraced by Formula 1 or it is a material selected from those embraced by Formula 2 and other materials listed below. The materials embranced by Formula 2 also can be used as wall forming materials. When the latter is selected from Formula 2, the stabilizer can be selected from the materials embraced by Formulae 1 or 2. Criterion that can be used for selecting the wall forming material and the stabilizing material from Formulae 1 and 2 and from other materials, are presented later in the specification.

The expressions "stabilizing material" and "wall forming stabilizing material" as used herein further include materials embraced by Formula 2 as follows:

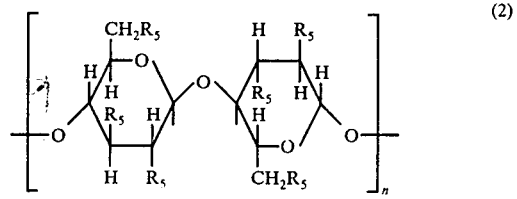

wherein $R_5$ is a member selected from the group consisting of hydroxyl; alkoxy; alkoxy substituted with a member selected from the group consisting of alkyl, alkoxy, halogen and cyano; alkylcarbonate; alkylcarbamate; alkylsulfonate; alkylsulfamate; oxalkyleneoxycarboalkyl; acyloxy including alkanoyloxy, alkenoyloxy and aroyloxy; alkanoyloxy substituted with an alkoxy, halogen, carboalkyl, carboalkoxy and cyanoalkoxy; aroyloxy substituted with a halo, carboxy, carboalkyl and cyano; furoyloxy, and $n$ is a positive integer greater than 5, usually 10 to $3 \times 10^6$.

Exemplary groups representative of $R_5$ of Formula 2 are as follows: by "alkyl" is meant straight or branched chain alkyl radicals of 1 to 20 carbon atoms inclusive, such as methyl, ethyl, n-propyl, iso-propyl, n-butyl, sec-butyl, pentyl, neo-pentyl, n-hexyl, iso-hexyl, heptyl, 4,4-dimethyl pentyl, 2,2,4-trimethylpentyl, and nonyl. By "alkenyl" is meant straight or branched chain alkenyl groups of 2 to 20 carbons such as 1-propenyl, 2-propenyl or allyl, 1-butenyl, 2-butenyl, 1-pentenyl, and the corresponding positional isomers such as 1-isobutenyl, 2-isobutenyl, 2-sec-butenyl, 2-methyl-1-butenyl, 2-methyl-2-pentyenyl and 2,3-dimethyl-3-hexenyl. The term "alkoxy" as used for $R_5$ included the straight and branched chain alkoxy groups having 1 to 20 carbons inclusive, for example, methoxy, ethoxy, propoxy, butoxy, n-pentoxy, n-hexoxy, isopropoxy, 2-butoxy, isobutoxy, 3-pentoxy, and n-octoxy. Exemplary halogen include fluorine, chlorine and bromine. Exemplary aryl include phenyl and naphthyl. Exemplary alkylene as a linking moiety within a substituent are alkylenes of 2 to 10 carbons such as 1,2-ethylene, 1,3-propylene, 1,2-propylene, 1,4-butylene, 1,5-pentylene, 1,6-hexylene, 1,7-heptylene and 1,10-decylene. Exemplary alkanoyloxy, alkenoyloxy and aroyloxy include formyloxy, acetyloxy, propionyloxy, valeryloxy, heptanoyloxy, octanoyloxy, undecanoyloxy, lauroyloxy, palmitoyloxy, stearoyloxy, oleoyloxy, acryloyloxy, methacryloyloxy, crotomyloxy, 3-butenoyloxy, benzoyloxy, phenylacetyloxy, cinnamoyloxy, naphthoyloxy, p-ethoxybenzyloxy, alloxyphenylacetyloxy, furoyloxy, p-nitrobenzoyloxy and chlorophenoxyacetyloxy.

The stabilizing and wall forming materials embraced by Formula 2 include polysaccharide materials having a degree of substitution on the anhydroglucose unit greater than from 0 up to 3 inclusive with the substituents at each $R_5$ the same or different. The materials can be polymeric cellulose esters or polymeric cellulose ethers. The repeating monomeric unit can be substituted with like ester groups, with different ester groups, with like ether groups, with different ether groups and with different ester and ether groups. Typical materials represented by Formula 2 include cellulose acetate acetoacetate, cellulose acetate chloroacetate, cellulose acetate furoate, dimethoxyethylcellulose acetate, cellulose acetate carboxymethoxypropionate, cellulose acetate phthalate, cellulose butyrate naphthylate, cellulose acetate benzoate, methylcellulose acetate, methylcyanoethyl cellulose, cellulose acetate methoxyacetate, cellulose acetate, cellulose acetate ethoxyacetate, cellulose acetate dimethylsulfamate, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate dimethylaminoacetate, cellulose triacetate, cellulose acetate ethyloxalate, mixed cellulose acetate laurate, cellulose butyrate furoate, cellulose stearate, cellulose resinate, cellulose acetate methylcarbonate, cellulose acetate ethylcarbonate, cellulose acetate methylcarbamate, and cellulose acetate ethylcarbamate.

The stabilizing and wall forming materials also include cellulose ethers such as alkylcellulose, methylcellulose, ethylcellulose, ethylmethylcellulose, hydroxyethylcellulose, hydroxypropylcellulose, hydroxyethyl methylcellulose, hydroxypropyl methylcellulose, ethylhydroxy ethylcellulose, hydroxybutyl methylcellulose, cyanoethylcellulose, benzylcellulose, sodium carboxymethylcellulose, sodium carboxymethylhydroxy ethylcellulose, carbamoylethylcellulose, carboxyethylcellulose, phenylcellulose, benzylhydrylcellulose, tritylcellulose, hexylpropylcellulose, carboxylbenzyl cellulose and 2-carboxylbenzoyloxy propylcellulose. Method for preparing the cellulose ethers are disclosed in Encyclopedia of Polymer Science and Technology, Vol. 3, pages 459 to 549, 1964, published by Interscience Publishers, Inc., New York.

Other materials useful as stabilizing materials and as wall forming materials include acrylated polysaccharides and acylated starches such as agar-agar acetate, acylated alginates, amylose triacetate, beta glucan acetate, beta glucan triacetate, acetyl alginate, triacetate of locust bean gum, alkanoyl carrageenin, acylated tragacanth, esterified gum karaya, cellulose derivatives substituted with an inorganic moiety such as a nitro group, hydroxylated ethylene vinylacetate, aromatic nitrogen containing polymeric materials that exhibit permeability to aqueous fluids and substantially no passage to solute, semipermeable membranes made from polymeric epoxides, copolymers of alkylene oxides and alkyl glycidyl ethers, polyvinyl acetate, cross-linked polyvinyl acetate, polyurethanes, film forming materials as disclosed by Loeb and Sourirajan in U.S. Pat. No. 3,133,132, cross-linked derivatives of polyvinyl alcohol, polyvinyl butyrate, mixtures of polyvinyl acetate and cellulose esters, ionically associated polyelectrolytes formed by the coprecipitation of a polycation and a polyanion as described in U.S. Pat. Nos. 3,276,586; 3,541,005; 3,541,006; 3,546,142; and 3,173,876; polystyrene derivatives such as poly(sodium styrene sulfonate) and poly(vinylbenzyltrimethyl ammonium chloride), polyesters, polyamides and polyacrylates. These materials and other materials are known to the art and disclosed in Handbook of Common Polymers by Scott, J. R. and Roff, W. J., 1971, published by CRC Press, Cleveland, Ohio.

Suitable wall forming materials for manufacturing an osmotic device can be selected from the above materials according to the criterion disclosed in U.S. Patent Application Ser. No. 440,281 filed Feb. 7, 1974, now U.S. Pat. No. 3,916,899. This criterion consists in first calculating for a membrane that is to be selected, the permeability to fluid necessary to deliver an amount of agent $Q_p$, in mg, in time $t$, in hours, from a device having a total membrane area A, in $cm^2$, a membrane thickness $h$, in mils, with the agent having a solubility in the fluid S, in mg/ml (solution), and the agent having an osmotic pressure in the device of $\pi$, in atm. The value $k$ is expressed in units $$\frac{cm^3}{cm^2} \cdot \frac{mil}{hr \cdot atm},$$

and it is calculated from Equation 1.

$$k = \frac{h}{SA} \cdot \frac{Q_p}{t} \cdot \frac{1}{\pi} \qquad (1)$$

Then, after having calculated the desired membrane permeability $k$ from Equation 1, laboratory measurements are made to identify a wall forming material capable of forming a membrane having a permeability $k_o$ substantially equivalent to the calculated permeability $k$. The measurements are carried out by using a standard osmosis cell and measuring the rate of fluid flow through a membrane made of wall forming material having a known composition and thickness. The flow rate is determined by measuring fluid transport from a first chamber containing a fluid free of agent through a membrane that separates it from a second chamber housing a solution containing a known concentration of agent that exhibits an osmotic gradient across the membrane. Sometimes the chamber contains an osmotically effective compound which is used as osmotic driving agent. The flow measurement is preformed by adding to the first chamber the fluid and then adding to the second chamber, equipped with a stirring bar, the same fluid containing agent, and optionally containing the additional osmotic agents. The first chamber is connected through a conduit to a reservoir containing a supply of fluid and the second chamber is connected to a vertically positioned tube of known diameter and calibrated with indicia that indicate the amount of fluid in the tube. In operation, fluid flows from the first chamber through the membrane into the second chamber by osmosis causing the solution to rise in the tube over time, $t$, to give a volume displacement, $\Delta V$, during a time interval, $\Delta T$. The volume, $\Delta V$, is read on the tube calibrated in $cm^3$, and the time interval, $\Delta t$, is measured with a stopwatch. The value $k_o\pi$ in $cm^3 \cdot mil/cm^2 \cdot hr$ for the membrane with permeability, $k_o$, for the agent solution with an osmotic pressure, $\pi$, is calculated from Equation 2, and wherein $A_o$ is the area of the membrane, in the diffusion cell, and $h_o$ is the thickness of this membrane.

$$k_o\pi = \frac{\Delta V}{\Delta t} \cdot \frac{h_o}{A_o} \qquad (2)$$

If the measured value, $k_o\pi$, approximates the calculated value, $k\pi$, the membrane can be used for manufacturing the osmotic device. Other procedures and devices useful for measuring fluid permeability and osmotic flow are disclosed in *J. App. Poly. Sci.*, Vol. 9, pages 1341 to 1362, 1965; and in *Yale J. Biol. Med.*, Vol. 42, pages 139 to 153, 1970.

Suitable stabilizing materials can be selected from the above materials for blending with the wall forming materials by those skilled in the art by using the procedures described below. These procedures are the membrane weight loss and the osmosis procedure. The procedures use membranes formed with stabilizers and formed without stabilizers. The membrane weight loss is carried out with membranes that are cast from solution or optionally melt pressed. The membranes are solution cast with a Gardner film-casting knife of a clean glass plate at room temperature with the solution removed by evaporation in an oven at elevated temperatures until the membranes are dry. Next, the membranes are removed from the glass and cut into strips 1 to 10 cm in length, 1 to 10 cm in width and having a thickness of 1 to 10 mils. Then, after all the strips are cut to have the same area and weight, they are placed in a glass container filled with a solution consisting of a known concentration of agent formulated with the fluid of the environment of use. The temperature of the container is made to correspond to the temperature of the environment where an osmotic device formed with the membranes will be placed for releasing agents. At regular time intervals, strips are taken form the solution, rinsed in distilled water, dried in an oven, usually 50° C for 24 hours, and weighed. The weight of a single strip repeatedly introduced into the solution, or the weight of many strips consecutively removed at different time intervals are indicated along the ordinate, plotted as a function of time indicated along the abscissa, such as $t_1$, $t_2$, $t_3$, etc. as shown in FIG. 7. In FIG. 7, line 1 represents the results obtained for a memrane that maintains its physical and chemical integrity when exposed to agent solution. That is, the membrane does not lose any weight over time and demonstrates inertness in the presence of agent solution. In the same figure, line 2 represents a membrane which upon exposure to agent solution, demonstrates a weight loss and is undesirable for making an osmotic device. A stabilizer can be blended into this membrane to enhance its inertness and substantially prevent weight loss thereby making the membrane useful for fabricating devices.

In the osmosis procedure, the rate of fluid flow through a membrane is measured and it is performed using an osmosis cell. The purpose of the procedure is to ascertain, (1) if a given membrane maintains its integrity in the presence of fluid and agent, and (2) if a stabilizer added to the membrane increases its physical and chemical integrity as seen from flux measurements. The procedure is carried out using the cell according to the above described procedure with the volume of solution, $\Delta V$, rising in the tube attached to chamber 2 measured and plotted as a function of time, $t$. The data obtained for two different membranes are shown in FIG. 8. In FIG. 8, line 1 represents a membrane that maintains its integrity in the presence of fluid and agent. That is, since the rate of fluid flow is substantially constant, the membrane does not undergo any substantial change over time, $t$. Line 2 shows the fluid flux, $\Delta V/\Delta t$, through a membrane where the rate is continually increasing over time. This change indicates the membrane does not maintain its integrity in the presence of fluid and agent. For those applications where a change in flux is unwanted, a stabilizer can be added to the membrane to enhance its inertness. The flux through membranes containing stabilizer is measured as just described.

Using the above techniques, one versed in the art would use the weight loss and osmosis procedures for ascertaining if the fluid and agent adversely effect the membrane and also for determining if a stabilizer blended into the membrane overcomes this effect. The stabilizer can be added in varying amounts to obtain an acceptable slope as seen in FIGS. 7 and 8, with the stabilizer decreasing the slope, not shown, indicating a lessening of membrane agent solution interaction.

Additional scientific criterious that can be used by those skilled in the art for selecting a stabilizing material include the following: (a) the material possesses a high degree of substitution, for example, the material has undergone etherification or esterification particularly acylation towards or to completion with membrane formed containing these stabilizers demonstrate increased resistance to hydrolysis and increased rejection of agent, (b) the stabilizer exhibits a flux decrease with increasing molecular size of the substituting group, such as an ether or ester group, (c) the stabilizer exhibits a flux decrease proportional to the increase in size of the substituent, for example, the decrease occurs at the number of carbon atoms increase in a hydrocarbon moiety such as an alkyl or alkoxy moiety, (d) the stabilizer exhibits increased stability with an increase in the degree of substitution of hydrophobic ether and larger hydrophobic ester groups with an accompanying decrease in the degree of substitution of smaller hydrophilic ester groups, and (e) the stabilizer exhibits a flux decrease as the number of polar, ionic groups bonded to the stabilizer decrease.

The expression "flux enhancing agent" as used herein means a compound that when added to a semipermeable wall forming material assists in regulating the fluid permeability or liquid flux through the wall. The agent can be preselected to increase or decrease the liquid flow through the wall. Agents that produce a marked increase in permeability to fluid such as water, are often essentially hydrophilic, while those that produce a marked decrease to fluids such as water, are essentially hydrophobic. The flux enhancer in some embodiments also can increase the flexibility of the wall. The flux enhancers, in one embodiment, are polyhydric alcohols and derivatives thereof, such as polyalkylene glycols of the formula $H\text{---}(O\text{-alkylene})_{\overline{n}}OH$ wherein the bivalent alkylene radical is straight or branched chain and has from 1 to 10 carbon atoms and $n$ is 1 to 500 or higher. Typical glycols include polyethylene glycols 300, 400, 600, 1500, 1540, 4000, and 6000 of the formula H—(OCH$_2$CH$_2$)$_n$—OH wherein $n$ is respectively 5 to 5.7, 8.2 to 9.1, 12.5 to 13.9, 29 to 36, 29.8 to 37, 68 to 84, and 158 to 204. Other polyglycols include the low molecular weight glycols such as polypropylene, polybutylene and polyamylene.

The flux enhancing agents in another embodiment include poly($\alpha$,107)-alkylenediols wherein the alkylene is straight or branched chain of from 2 to 10 carbon atoms such as poly(1,3)-propanediol, poly(1,4)-butanediol, poly(1,5)-pentanediol and poly(1,6)-hexanediol. The diols also include aliphatic diols of the formula HOC$_n$H$_{2n}$OH wherein $n$ is from 2 to 10 and the diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux enhancers include esters and polyesters of alkylene glycols of the formula HO—(alkylene-O—)$_n$H wherein the divalent alkylene radical includes the straight chain groups and the isomeric forms thereof having from 2 to 6 carbons and $n$ is 1 to 14. The esters and polyesters are formed by reacting the glycol with either a monobasic or dibasic acid. Exemplary flux enhancers are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid and polyester or triethylene glycol with adipic acid. Also, certain stabilizers in some embodiments can serve as a flux enhancer particularly when it has a low D.S. of acyl moieties.

Figure 9:
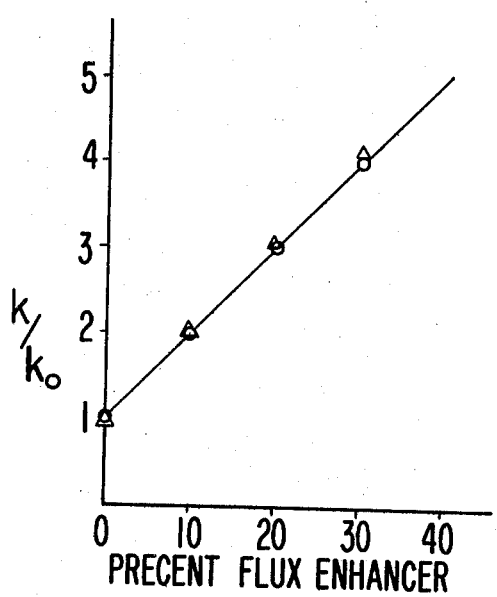
FIG. 9 represents the increase in fluid permeability of a material containing a flux enhancer.

Suitable flux enhancers for compounding with a material to increase its fluid permeability can be selected by blending known amounts of an enhancer with the material, casting the blends into thin films, and then measuring the increase in permeability towards the fluid found in the environment of use. For example, to two separate batches of wall forming cellulose acetate having an acetyl content of 32% and 39.8% were added 1, 2 and 3 grams of flux enhancer polyethylene glycol having a molecular weight of 400 and the ingredients blended in a high shear blender in the presence of 120 ml of dimethyl formamide to yield six blends. Next, the blends were solvent cast with a Gardener knife and dried in an oven for 7 days at 50° C. The water permeability of the six films was measured in the osmosis cell described above and the results recorded in FIG. 9. In the figure, the triangle represents cellulose acetate 32% and the circle represents cellulose acetate 39.8%. Also, as recorded on the ordinate, $k_o$ indicates the water permeability through cellulose acetate 32% free of flux enhancer and cellulose acetate 39.8% that did not contain any flux enhancer, and $k$ indicates the water permeability through cellulose acetate 32% and cellulose acetate 39.8% where both contained the flux enhancer. The positive integers 10, 20, 30 and 40 recorded on the abscissa, indicate the percent of flux enhancer in the film. Using the above technique, specific flux enhancers for blending with specific materials to regulate the permeability can be selected for making the desired osmotic device. The amount of flux enhancer added to a material generally is an amount sufficient to produce the desired permeability, and it will vary according to the wall forming material and the flux enhancer used to regulate the permeability. Usually, from 0.001 parts up to 50 parts, or higher of flux enhancer can be used to achieve the desired results, with a presently preferred range consisting of 0.1 part up to 30 parts of enhancer or mixtures thereof for 100 parts of wall forming material.

Exemplary plasticizers suitable for the present purpose generically include plasticizers that lower the temperature of the second-order phase transition of the wall or the elastic modulus thereof; and also increase the workability of the wall, its flexibility and its permeability to fluid. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, sulfonamides, and halogenated phenyls. Generally from 0.01 to 100 parts, or higher, of a plasticizer or a mixture of plasticizers are incorporated into 100 parts of wall forming material.

Exemplary plasticizers include dialkyl phthalates, dicycloalkyl phthalates, diaryl phthalates and mixed alkyl-aryl phthalates as represented by dimethyl phthalate, dipropyl phthalate, di(2-ethylhexyl)-phthalate, diisopropyl phthalate, diamyl phthalate and dicapryl phthalate; alkyl and aryl phosphates such as tributyl phosphate, trioctyl phosphate, tricresyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di(2-methoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phythayl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Other plasticizers include camphor, N-ethyl-(o- and p-toluene) sulfonamide, chlorinated biphenyl, benzophenone, N-cyclohexyl-p-toluene sulfonamide, and substituted epoxides.

Suitable plasticizers can be selected for blending with the wall forming materials by selecting plasticizers that have a high degree of solvent power for the materials, are compatible with the materials over both the processing and use temperature range, exhibits permanence as seen by its strong tendency to remain in the plasticized wall, imparts flexibility to the material and are non-toxic to animals, humans, avians, fishes and reptiles. Produces for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter $\delta$, the Flory-Huggins interaction parameter $\mu$, and the cohesive-energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the materials. Usually about 0.001 parts up to 50 parts, or higher, plasticizer can be used for 100 parts of wall forming material with a presently preferred range of 0.1 part to 20 parts of plasticizer, or mixtures thereof for 100 parts of wall forming materials.

Dispersants useful for the present purpose are those dispersants when added to a wall forming material and other materials aid in producing an integral composite that is useful for making the operative wall of a device. The dispersants act by regulating the surface energy of materials to improve their blending into the composite. This latter material is used for manufacturing devices that maintain there integrity in the environment of use during the agent release period. Generally, the dispersants are amphipathic molecules comprises of a hydrophobic part and a hydrophilic part. The dispersants can be anionic, cationic, nonionic or amphoteric and they include anionics such as sulfated esters, amides, alcohols, ethers and carboxylic acids; sulfonated aromatic hydrocarbons, aliphatic hydrocarbons, esters and ethers; acylated amino acids and peptides; and metal alkyl phosphates; cationic dispersants such as primary, secondary, tertiary and quaternary alkylammonium salts; acylated polyamines; and salts of heterocyclic amines, arylammonium dispersants such as esters of polyhydric alcohols, alkoxylated amines; polyoxyalkylene; esters and ethers of polyoxyalkylene glycols; alkanolamine fatty acid condensates; tertiary acetylamic glycols; and dialkyl polyoxyalkylene phosphates; and ampholytics such as betamines; and amino acids.

Typical dispersants include polyoxyethylenated glycerol ricinoleate; polyoxyethylenated caster oil having from 9 to 52 moles of ethylene oxide; glycerol mannitan laurate, and glycerol (sorbitan oleates, stearates or laurates); polyoxyethylenated sorbitan laurate, palmitate, stearate, oleate or hexaolate having from 5 to 20 moles of ethylene oxide; mono-, di- and poly-ethylene glycol stearates, laurates, oleates, myristates, behenates or ricinoleates; propylene glycol carboxylic acid esters; sorbitan laurate, palmitate, oleate, and stearate; polyoxyethylenated octyl, nonyl, decyl, and dodecylphenols having 1 to 100 moles of ethylene oxide; polyoxyethylenated nonyl, lauryl, decyl, cetyl, oleyl and stearyl alcohols having from 3 to 50 moles of ethylene oxide; polyoxypropylene glycols having from 3 to 300 moles of ethylene oxide; sodium salt of sulfated propyl oleate; sodium di(heptyl)sulfosuccinate; potassium xylenesulfonate; 1:1 myristic acid diethanolamide; N-coco-β-aminopropionic acid; bis(2-hydroxyethyl)tallowamine oxide; (diisobutylphenoxyethoxyethyl)dimethylbenzylammonium halide; N,N'-polyoxypropylenated ethylenediamine having a molecular weight from 500 to 3000; tetraalkylammonium salts with up to 26 carbon atoms in the cation; sodium or potassium salt of polypeptide cocoanut, oleic or undecylenic acid condensate; metal salts of N-acylated short chain aminosulfonic acids; soybean phosphatides; and sulfobetaine.

Suitable dispersants can be selected from the above and from other dispersants for blending with wall forming materials by using the dispersant's hydrophile-lipophile balance number, HLB. This number represents the proportion between the weight percentages of hydrophilic and lipophilic groups in a dispersant. In use, the number indicates the behavior of the dispersant, that is, the higher the number the more hydrophilic the dispersant and the lower the number the more lipophilic the dispersant. The required HLB number for blending wall forming materials is determined by selecting a dispersant with a known number, blending it with the materials and observing the results. A homogenous composite is formed with the correct number; while a heterogenous mixture indicates a different number is needed. This new number can be selected by using the prior number as a guide. The HLB number is known to the art for many dispersants, and they can be experimentally determined according to the procedure in *J. Soc. Cosmetic Chem.*, Vol. 1, pages 311 to 326, 1949, or it can be calculated by using the procedure in *J. Soc. Cosmetic Chem.*, Vol. 5, pages 249 to 256, 1954, and in *Am. Perfumer Essent. Oil Rev.*, Vol. 65, pages 26 to 29, 1955. Typical HLB numbers are set forth in Table 1. Generally a number of 10 or less indicates lipophilic behavior and 10 or more indicates hydrophilic behavior. Also, HLB numbers are algebraically additive. Thus, by using a low number with a higher number, blends of dispersants can be prepared having numbers intermediate between the two numbers. The amount of dispersant needed is an amount that when blended with all forming materials will form the desired wall composite, and it will vary according to the particular dispersant and materials that are blended to form the wall. Generally, the amount of dispersant will range from about 0.001 parts up to 40 parts, or higher, for 100 parts of wall forming material with a presently preferred range of 0.1 part to 15 parts of dispersant or mixtures thereof, for 100 parts of wall forming material.

TABLE 1

| DISPERSANT | HLB NUMBER |
|---|---|
| Sorbitan trioleate | 1.8 |
| Polyoxyethylene sorbitol beeswax | 2.0 |
| Sorbitan tristearate | 2.1 |
| Polyoxyethylene sorbitol hexastearate | 2.6 |
| Ethylene glycol fatty acid ester | 2.7 |
| Propylene glycol fatty acid ester | 3.4 |
| Propylene glycol monostearate | 3.4 |
| Ethylene glycol fatty acid ester | 3.6 |
| Glycerol monostearate | 3.8 |
| Sorbitan monooleate | 4.3 |
| Propylene glycol monolaurate | 4.5 |
| Diethylene glycol fatty acid ester | 5.0 |
| Sorbitan monopalmitate | 6.7 |
| Polyoxyethylene dioteate | 7.5 |
| Polyoxypropylene mannitol dioleate | 8.0 |
| Sorbitan monolaurate | 8.6 |
| Polyoxyethylene lauryl ether | 9.5 |
| Polyoxyethylene sorbitan monolaurate | 10.0 |
| Polyoxyethylene lanolin derivative | 11.0 |
| Polyoxyethylene glycol 400 monooleate | 11.4 |
| Triethanolamine oleate | 12.0 |
| Polyoxyethylene nonyl phenol | 13.0 |
| Polyoxyethylene sorbitan monolaurate | 13.3 |
| Polyoxyethylene sorbitol lanolin | 14.0 |
| Polyoxyethylene stearyl alcohol | 15.3 |
| Polyoxyethylene 20 cetyl ether | 15.7 |
| Polyoxyethylene 40 stearate | 16.9 |
| Polyoxyethylene monostearate | 17.9 |
| Sodium oleate | 18.0 |
| Potassium oleate | 20.0 |

Exemplary solvents suitable for manufacturing the composite wall include inert inorganic and organic solvents that do not adversely harm the wall forming materials and the final composite wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

The expression "passageway" as used herein comprises means and methods suitable for releasing the agent from the device. The expression includes an aperture, orifice or bore through the wall formed by mechanical procedures or by eroding an erodible element, such as a gelatin plug, in the environment of use. A detailed description of osmotic passageways and the maximum and minimum dimensions for a passageway are disclosed in U.S. Pat. No. 3,845,770 and in U.S. Patent Application Ser. No. 440,281 filed Feb. 7, 1974, now U.S. Pat. No. 3,916,899.

The osmotically effective compounds that can be used for the purpose of the invention include inorganic and organic compounds that exhibit an osmotic pressure gradient against an external fluid across the composite wall of the device. The compounds are used mixed with an agent that has limited solubility in the external fluid with the compound forming a saturated solution containing agent that is osmotically delivered from the device. The phrase "limited solubility" as used herein means the agent has a solubility of about less than 1% by weight in the external fluid. The compounds are used by homogenously or heterogenously mixing the compound or a mixture of compounds with an agent, either before they are charged into the reservoir, or by self-mixing after they are charged into the reservoir. In operation, these compounds attract fluid into the device producing a solution of compound which is delivered from the device concomitantly transporting undissolved and dissolved agent to the exterior of the device. Osmotically effective compounds useful for the present purpose include magnesium sulfate, magnesium chloride, sodium chloride, lithium chloride, potassium sulfate, sodium carbonate, sodium sulfite, lithium sulfate, potassium chloride, calcium bicarbonate, sodium sulfate, calcium sulfate, potassium acid phosphate, calcium lactate d-mannitol, urea, inositol, magnesium succinate, tartaric acid, carbohydrates such as raffinose, sucrose, glucose, α-d-lactose monohydrate, and mixtures thereof. The compound is initially present in excess and it can be in any physical form such as particle, crystal, pellet, tablet, strip, film or granule. The osmotic pressure of saturated solutions of various osmotically effective compounds and for mixtures of compounds at 37° C, in water, is listed in Table 2. In the table, the osmotic pressure $\pi$, is in atmospheres, ATM. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table 2, osmotic pressures of from 20 ATM to 500 ATM are set forth; of course, the invention includes the use of lower osmotic pressures from zero, and higher osmotic pressures than those set forth by way of example in Table 2. The osmometer used for the present measurements is identified as Model 302B, Vapor Pressure Osmometer, manufactured by the Hewlett Packard Co., Avondale, Penna.

TABLE 2

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Sucrose | 150 |
| Mannitol-Lactose | 130 |
| Dextrose | 82 |
| Potassium Sulfate | 39 |
| Mannitol | 38 |
| Sodium Phosphate Tribasic . 12$H_2O$ | 36 |
| Sodium Phosphate Dibasic . 7$H_2O$ | 31 |
| Sodium Phosphate Dibasic . 12$H_2O$ | 31 |
| Sodium Phosphate Dibasic Anhydrous | 29 |
| Sodium Phosphate Monobasic . $H_2O$ | 28 |

The expressive "active agent" as used herein broadly includes any compound, composition of matter or mixture thereof, that can be delivered from the device to produce a beneficial and useful result. The agent can be soluble in a fluid that enters the reservoir and functions as an osmotically effective solute or it can have limited solubility in the fluid and be mixed with an osmotically effective compound soluble in fluid that is delivered from the device. The active agent includes pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, micro-organism attenuators, and other agents that benefit the environment of use.

In the specification and the accompanying claims, the term "drug" includes any physiologically or pharmacologically active substance that produces a localized or systemic effect or effects in animals, including mammals, humans and primates, avians, domestic household, sport or farm animals such as sheep, goats, cattle, horses and pigs, for administering to laboratory animals such as mice, rats and guinea pigs, and to fishes, reptiles and zoo animals. The active drug that can be delivered includes inorganic and organic compounds without limitation, those materials that act on the cental nervous system such as hypnotics and sedatives, including pentobarbital sodium, phenobarbital, secobarbital, thiopental and mixtures thereof, heterocyclic hypnotics such as dioxopiperidines and glutarimides, hypnotics and sedatives such as amides and ureas, exemplified by diethylisovaleramide and α-bromoisovaleryl urea, hypnotic and sedative urethanes and disulfanes, psychic energizers such as isocarboxazid, nialamide, phenelzine, imipramine, tranylcypromide and paragylene, tranquilizers such as chloropromazine, promazine, fluphenazine, reserpine, deserpidine, meprobamate, benzodiazepines such as chlordiazepoxide, anticonvulsants such as primidone, enitabas, diphenylhydantoin, ethltion, pheneturide and ethosuximide, muscle relaxants and antiparkinson agents such as mephenesin, methocarbomal, trihexylphenidyl, biperiden, levo-dopa also known as L-dopa and L-$\beta$-3-4-dihydroxypehnylalanine, analgesics such as morphone, codeine, meperidine, nalorphine, antipyretics and anti-inflammatory agents such as aspirin, salicylamide, colchicine and sodium salicylamide, local anesthetics such as procaine, lidocaine, naepaine, piperocaine, tetracaine and dibucane, antispasmodics and muscle contractants such as atropine, scopolamine, methscopolamine, oxyphenonium, papaverine, prostaglandins such as $PGE_1$, $PGE_2$, $PGF_{1\alpha}$, $PGF_{2\alpha}$ and PGA, anti-microbials such as penicillin, tetracycline, oxytetracycline, chlorotetracycline, chloramphenicol and sulfonamides, anti-malarials such as 4-aminoquinolines, 8-aminoquinolines and pyrimethamine, hormonal agents such as prednisolone, cortisone, cortisol and triamcinolone, androgenic steroids such as methyltestosterone, and fluoxmesterone, estrogenic steroids such as 17$\beta$-estradiol, $\alpha$-estradiol, estriol, $\alpha$-estradiol 3-benzoate, and 17-ethynyl estradiol-3-methyl ether, progestational steroids such as progesterone, 19-nor-pregn-4-ene-3,20-dione, 17-hydroxy-19-nor-17-$\alpha$-pregn-5(10)-ene-20-yn-3-one, 17$\alpha$-ethynyl-17-hydroxy-5(10)-estren-3-one, and 9$\beta$,10$\alpha$-pregna-4,6-diene-3,20-dione, sympathomimetic drugs such as epinephrine, amphetamine, ephedrine and norepinephrine, cardiovascular drugs such as procainamide, procainamide hydrochloride, amyl nitrile, nitroglycerin, dipyredamole, sodium nitrate and mannitol nitrate, diuretics such as chlorathiazide, acetazolamide, methazolamide and flumethiazide, antisparasitics such as bephenium, hydroxynaphthoate, dichlorophen and dapsone, neoplastics such as mechlorethamine, uracil mustard, 5-fluorouracil, 6-thioguanine and procarbazine, hypoglycemic drugs such as insulin, isophane insulin, protamine zinc insulin suspension, globin zinc insulin, extended insulin zinc suspension, tolbutamide, acetohexamide, tolazamide and chloropropamide, nutritional agents such as ascorbic acid, niacin, nicotinamide, folic acid, choline, biotin, pantothenic acid, and vitamin $B_{12}$, essential amino acids, essential fats, eye drugs such as pilocarpine, pilocarpine salts such as pilocarpine nitrate,, pilocarpine hydrochloride, dichlorphenamide, atropine, atropine sulfate, scopolamine and eserine salicylate, and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumurate and sodium lactate. The beneficial drugs are known to the art in *Remington's Pharmaceutical Sciences*, 14th Ed., 1970, published by Mack Publishing Co., Easton, Penna.; and in *The Pharmacological Basis of Therapeutics*, by Goodman and Gilman, 4th Ed., 1970, published by The MacMillian Company, London.

The drug can also be in various forms, such as uncharged molecules, molecular complexes, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides which have solubility characteristic suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir as a solution, dispersion, paste, cream, particle, granule, emulsion, suspension or powder. Also, the agent can be mixed with a binder, dispersant, emulsifier or wetting agent and dyes.

The amount of agent present in the device is initially in excess of the amount that can be dissolved in the fluid that enters the reservoir. Under this physical state when the agent is in excess, the device will osmotically operate to give a substantially constant rate of release. The rate of agent release pattern can also be varied by having different amounts of agent in the reservoir to form solutions containing different concentrations of agent for delivery from the device. Generally, the device can house from 0.05 ng to 5 grams or more, with individual devices containing for example, 25 ng, 1 mg, 5 mg, 250 mg, 500 mg, 1.5 g, and the like.

The solubility of an agent in an external fluid can be determined by various art known techniques. One method consists in preparing a saturated solution comprising the external fluid plus the agent as ascertained by analyzing the amount of agent present in a definite quantity of the fluid. A simple apparatus for this purpose consists of a test tube of medium size fastened upright in a water bath maintained at constant temperature and pressure, for example, one atmosphere, in which the fluid and agent are placed and stirred by a motor driven rotating glass spiral. After a given period of stirring, a definite weight of the fluid is analyzed and the stirring continued for an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed; if the agent has limited solubility in the fluid, then an osmotically effective compound can be incorporated into the device. Numerous other methods are available for the determination of the solubility of an agent in a fluid. Typical methods used for the measurement of solubility are chemical analysis, ultra violet spectometry, density, refractive index and electrical conductivity. Details of various methods for determining solubilities are described in *United States Public Health Service Bulletin*, No. 67 of the Hygienic Laboratory; *Encyclopedia of Science and Technology*, Vol. 12, pages 542 to 556, 1971, published by McGraw-Hill, Inc.; and *Encyclopaedic Dictionary of Physics*, Vol. 6, pages 547 to 557, 1962, published by Pergamon Press, Inc.

The devices of the invention are manufactured by standard techniques. For example, in one embodiment, the agent and other ingredients that may be housed in the compartment and a solvent are mixed into a solid, semisolid or gel form by conventional methods such as ballmilling, calendering, stirring, or rollmilling and then pressed into a preselected shape. The wall forming the devices can be applied by molding, spraying or dipping the pressed shape into wall forming materials. In another embodiment, a wall can be cast into a film, shaped to the desired dimensions, partially sealed to define a hollow compartment that is filled with agent and then closed. The device also can be manufactured with an empty compartment that is filled through the passageway. High frequency electronic techniques can be used to provide devices with walls having clean edges. Another, and presently preferred, technique that can be used is the air suspension procedure. This procedure consists in suspending and tumbling the pressed agent in a current of air and the wall forming composite until the wall is applied to the agent. The air suspension procedure is described in U.S. Pat. No. 2,799,241; *J. Am. Pharm. Assoc.*, Vol. 48, pages 451 to 459, 1959; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remingon, Fourteenth Edition, pages 1626 to 1678, 1970, published by Mack Publishing Company, Easton, Penna.

The following examples are merely illustrative of the present invention, and they should not be considered as limiting the scope of the invention in any way, as these examples and other equivalents thereof will become apparent to those varied in the art in the light of the present disclosure, the drawings and the accompanying claims.

EXAMPLE 1

The permeability of a series of walls formed of blends of materials was illustrated by preparing and measuring their permeability to water as follows: To a first mixture consisting of 76.6 parts of wall forming cellulose acetate having an acetyl content of 38.3% and 12.76 parts of the flux enhancer polyethylene glycol having a molecular weight of 400 dissolved in a solvent consisting of 80 parts of methylene chloride and 20 parts of methanol was added in small amounts and with continuous stirring a second mixture consisting of 8.52 parts hydroxybutyl methylcellulose which functions as both a stabilizer and a flux enhancer and 2.12 parts of the dispersant polyoxypropylene glycol having a molecular weight of 950 dissolved in a solvent consisting of 80 parts methylene chloride and 20 parts of methanol and the stirring continued until the two mixtures were thoroughly blended. Then, an additional solvent consisting of 90 parts of acetone and 10 parts of water was added to the blend and all the materials stirred for 30 minutes at room temperature, 22° C, and atmosphere pressure until a homogeneous composite was formed.

Next, a film of 2.5 mils (dry thickness) of the composite was cast with a Gardner film-casting blade on a borosilicate glass substrate warmed to 40° C. The film was dried while on the substrate in an oven at 70° C for 120 hours. Then, the film was stripped from the substrate and it was observed to be optionally clear. The water transmission rate of the film was measured using potassium chloride and sodium acetazolamide in the osmosis cell at 37° C, and the results recorded in FIG. 10, discussed below.

EXAMPLE 2

The procedure of Example 1 was repeated in this example and all conditions were as described except that the film consisted of 68.10 parts of cellulose acetate having an acetyl content of 38.3%, 17.02 parts of hydroxybutyl methylcellulose, 12.76 parts of polyethylene glycol having a molecular weight of 400 and 2.12 parts of polyoxypropylene glycol having a molecular wieght of 950. The permeability of the film to water using the same osmotic attractants was measured and the results recorded in FIG. 10, discussed below.

EXAMPLE 3

The procedure of Example 1 was repeated in this example with all conditions as described except that the film consisted of 59.60 parts of cellulose acetate having an acetyl content of 38.3%, 25.52 parts of hydroxybutyl methylcellulose, 12.76 parts of polyethylene glycol having a molecular weight of 400 and 2.12 parts of polyoxypropylene glycol having a molecular weight of 950. The permeability of the film to water using the same osmotic attractants was measured and the results recorded in FIG. 10.

Figure 10:
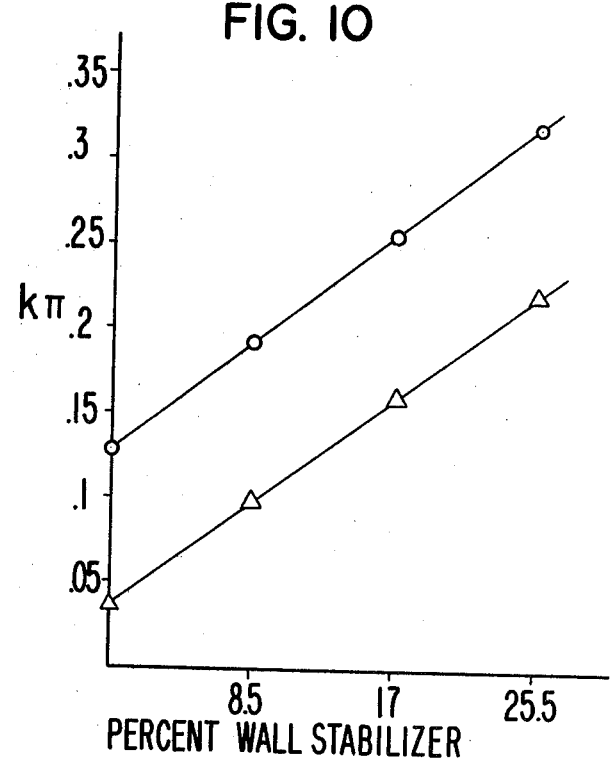
FIG. 10 represents the fluid permeability of films as a function of increased amounts of a flux enhancer which act as a wall stabilizer at the same time.

In FIG. 10, the permeabilities through the films prepared according to Examples 1, 2 and 3 are plotted as a function of the hydroxybutyl methylcellulose content of the film. The numbers on the abscissa represent the percent of wall stabilizer hydroxybutyl methylcellulose in the three films, and the numbers or the ordinate represent the permeability $k\pi$ ($cm^3 \cdot mil/cm^2 \cdot hr$) through the films. The line with the circles indicates potassium chloride as the osmotic attractant and the lines with triangles indicates sodium acetazolamide as the attractant.

EXAMPLE 4

Figure 11:
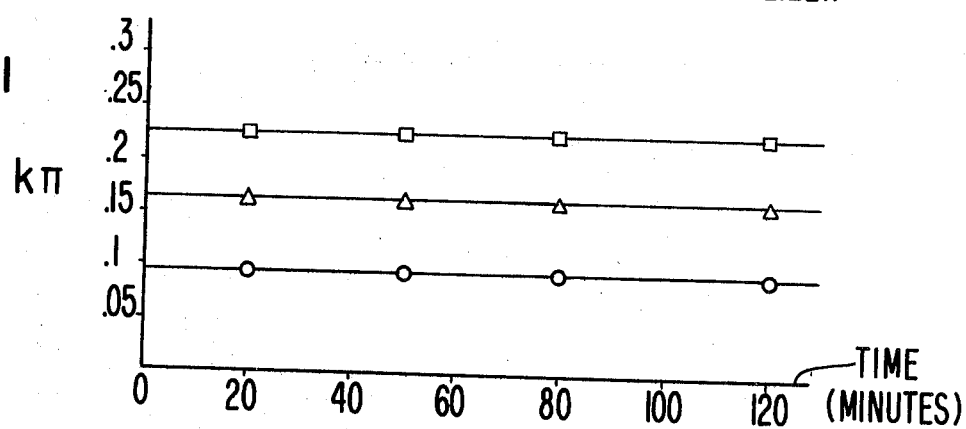
FIG. 11 is a graph indicating the stability of films in the presence of an agent.

The stability of a series of walls formed of blends of materials was demonstrated by preparing the walls and measuring their stability in the presence of an osmotic attractant. The walls used were prepared according to the procedures of Examples 1, 2 and 3. Their stability was determined by measuring their permeability to water using sodium acetazolamide as the osmotic attractant in osmosis cells at 37° C. The results are plotted in FIG. 11. In the figure the numbers on the abscissa represent the time in minutes the film is in contact with a saturated solution of sodium acetazolamide and the numbers on the ordinate represent the water transmission rate, $k\pi$ ($cm^3 \cdot mil/cm^2 \cdot hr$), through the film. The line with circles represents a film prepared according to Example 1. The line with triangles represents a film prepared according to Example 2. The line with squares represents a film prepared according to Example 3.

EXAMPLE 5

The inertness (physical and chemical stability) in the presence of a caustic-acting osmotic attractant, and the permeability to an aqueous medium of a series of composite walls as a function of the degree of substitution of the wall forming material and the concentration of the stabilizer and flux enhancer in the wall were determined by preparing and analyzing the walls according to the procedure of Example 1. The results obtained are presented in Table 3. In the table, the meaning of the terms and the abbreviations is as follows: the number in the column headed, "Walls", indicates a series of composite walls and the small letters within a series indicates the different compositions of particular walls made in a series; the term "Composition" indicates the materials and percent thereof for the walls; (the letters in a series refer to embodiments of the compositions in a series and when they are used, they indicate an ingredient that is present in different amounts). In the table, the representations are as follows: in compositions 1 through 3, the number 85.12 indicates the amount of cellulose acetate or a blend of cellulose acetate plus the amount of H.B.M.C. present in a composition; the expression $(85.12 - x)\%$ indicates the percent cellulose acetate present as a single ingredient or as a blend of cellulose acetates, and $x$ indicates the percent H.B.M.C. present in each composition; in composition 4 the number 72.38 indicates the amount of cellulose acetate plus the amount of P.E.G. present in a composition; the expression $(72.38 - x)\%$ indicates the present cellulose acetate present, and x is the percent P.E.G.; "C.A." means cellulose acetate; "D.S." is the degree of substitution; "H.B.M.C." is hydroxybutyl methylcellulose; "P.E.G." and "polyethylene glycol" indicate polyethylene glycol having a molecular weight of 400; "Polyoxypropylene glycol" indicates the dispersant having a molecular weight of 950; "$K_2SO_4$" is potassium sulfate having an osmotic pressure of 39 atmospheres; "T.M." is the caustic-acting osmotic attractant theophylline monoethanolamine having an osmotic pressure of 55 atmospheres; and "$k\pi$" is the water transmission of the wall measured in $cm^3.mil/cm^2.hr$.

TABLE 3

| Wall | Composition | Osmotic Attractant | $k\pi$ |
|---|---|---|---|
| 1 | Cellulose acetate D.S. 1.75 (85.12 − x)%, plus Polyethylene glycol 12.76%, Polyoxypropylene glycol 2.12%, and Hydroxybutyl methylcellulose x%. | | |
| | a) C.A. 76.60% + H.B.M.C. 8.52% | $K_2SO_4$ | 0.15 |
| | b) C.A. 68.10% + H.B.M.C. 17.02% | $K_2SO_4$ | 0.20 |
| | c) C.A. 59.60% + H.B.M.C. 25.52% | $K_2SO_4$ | 0.25 |
| 2 | Cellulose acetate consisting of a blend of 67.19% Cellulose acetate with D.S. 1.75 and 32.81% Cellulose acetate with D.S. 2.3 (85.12 − x)%, plus Polyethylene glycol 12.76%, Polyoxypropylene glycol 2.12%, and Hydroxybutyl methylcellulose x%. | | |
| | a) C.A. 76.60% + H.B.M.C. 8.52% | T.M. | 0.13 |
| | b) C.A. 68.10% + H.B.M.C. 17.02% | T.M. | 0.18 |
| | c) C.A. 59.60% + H.B.M.C. 25.52% | T.M. | 0.215 |
| 3 | Cellulose acetate consisting of a blend of 50% Cellulose acetate with D.S. 1.75 and 50% Cellulose acetate with D.S. 2.3 (85.12 − x)%, plus Polyethylene glycol 12.76%, Polyoxypropylene glycol 2.12%, Hydroxybutyl methylcellulose x%. | | |
| | a) C.A. 76.60% + H.B.M.C. 8.52% | T.M. | 0.1 |
| | b) C.A. 68.10% + H.B.M.C. 17.02% | T.M. | 0.14 |
| | c) C.A. 59.60% + H.B.M.C. 25.52% | T.M. | 0.17 |
| 4 | Cellulose acetate D.S. 1.75, (72.38 − x)%, plus Hydroxybutyl methylcellulose 25.5%, Polyoxypropylene glycol 2.12%, and Polyethylene glycol, x%. | | |
| | a) C.A. 66.38% + P.E.G. 6.00% | $K_2SO_4$ | 0.144 |
| | b) C.A. 59.63% + P.E.G. 12.75% | $K_2SO_4$ | 0.24 |
| | c) C.A. 56.48% + P.E.G. 15.90% | $K_2SO_4$ | 0.27 |
| | d) C.A. 46.88% + P.E.G. 25.50% | $K_2SO_4$ | 0.31 |
| 5 | 64% Cellulose acetate blend of 67.19% Cellulose acetate with D.S. 1.75 and 32.81% Cellulose acetate with D.S. 2.3, Hydroxybutyl methylcellulose 22%, Polyethylene glycol 12%, and Polyoxypropylene glycol 2%. | T.M. | 0.19 |

EXAMPLE 6

The permeability of a film consisting of at least two cellulose acetates each having a different acetyl content was determined by preparing a film and measuring its permeability according to the procedure of Example 1. The cellulose acetates used had an acetyl content ranging from 23% to 44.8% and the amount used ranged from 0.1% to 99.9% of a cellulose acetate having an acetyl content of from 23% up to 32% and from 99.9% to 0.1% of a cellulose acetate having an acetyl content from 32% up to 44.8%. A plurality of films were prepared according to the example and they had the following composition:

(a) a film comprising 85.12% cellulose acetate blend consisting of 67.19% cellulose acetate having an acetyl content of 32% and 32.81% cellulose acetate having an acetyl content of 38.3%, 12.76% polyethylene glycol having a molecular weight of 400 and 2.12% polyoxypropylene glycol having a molecular weight of 950;

(b) a film comprising 76.60% cellulose acetate of the blend as set forth in (a), polyethylene glycol and polyoxypropylene glycol the same as in (a), and additionally, 8.52% of hydroxybutyl methycellulose;

(c) a film comprising 68.10% cellulose acetate blend of (a), polyethylene glycol and polyoxypropylene glycol the same as (a), and 17.02% of hydroxybutyl methylcellulose; and, (d) a film comprising 59.60% cellulose acetate blend of (a), polyethylene glycol and polyoxypropylene glycol the same as (a), and 25.52% of hydroxybutyl methylcellulose.

Figure 12:
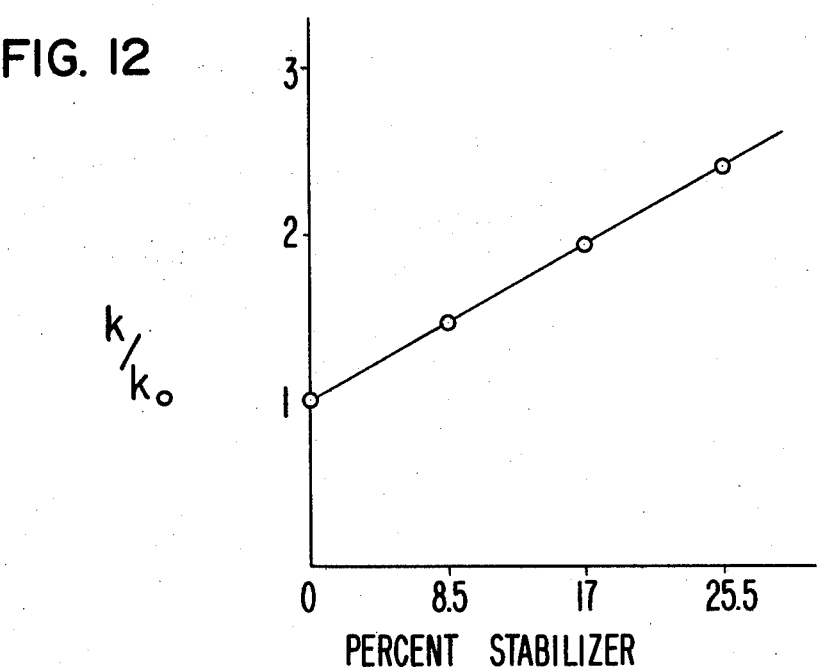
FIG. 12 is a graph indicating the fluid permeability of a film comprised of at least two wall forming materials.

The ratio of the permeability of the films to water is plotted in FIG. 12. In this figure, the numbers along the abscissa represent the percent hydroxybutyl methylcellulose in the film and the numbers along the ordinate indicate the permeability ratio $k/k_o$. The values for $k/k_o$ were obtained by dividing the measured permeability of film (a) into each of (a), (b), (c), and (d) thereby expressing the permeability ratio of the films as a function of their hydroxybutyl methylcellulose content. In the figures, $k_o$ is the permeability of the film to water with the film containing a zero concentration of H.B.M.C.

EXAMPLE 7

Figure 13:
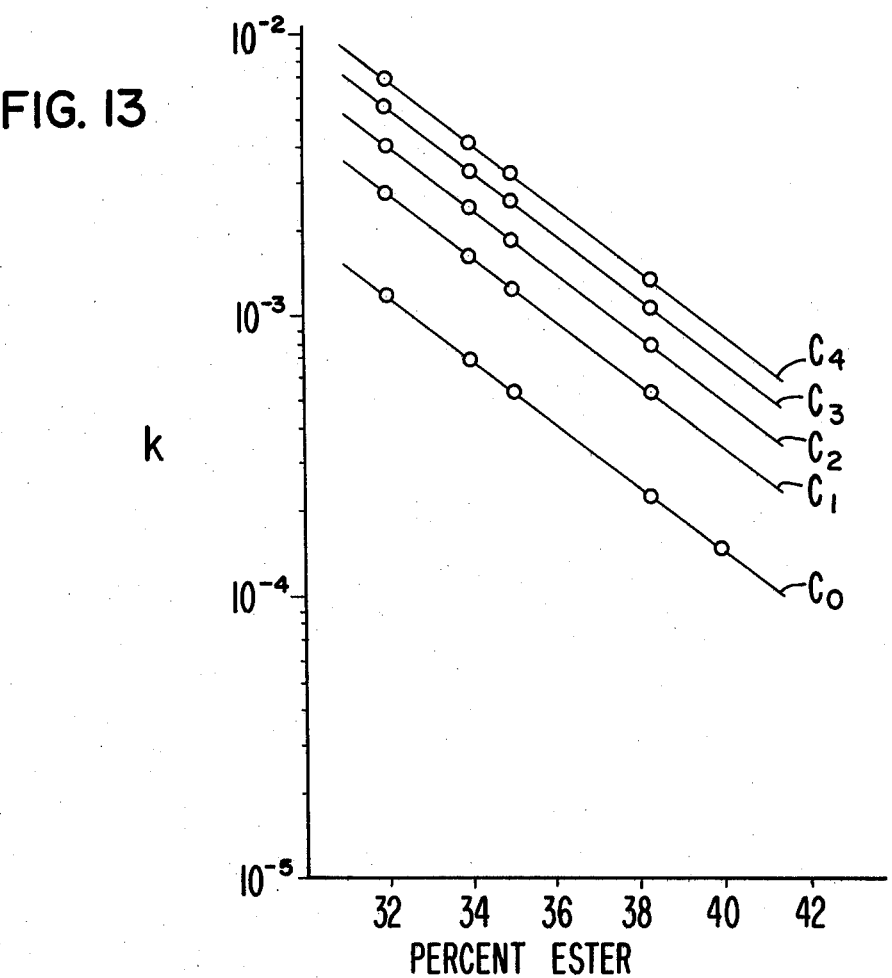
FIG. 13 is a graph indicating the fluid permeability of a series of films as a function of one of the substituting groups covalently bonded to a film forming material.

The fluid permeability of cellulose acetate films as a function of the acetyl content of each film in the presence of increasing amounts of hydroxybutyl methylcellulose was determined by preparing a multiplicity of films and measuring their permeability to water. The films were made and the water transmission of each film measured by following the procedures of Examples 1 and 6. The results obtained were recorded in FIG. 13. In this figure the number along the abscissa represents the ester content; that is, the percent acetyl content of the films, and the numbers along the ordinate represent the fluid permeability $k$ expressed as $cm^3.mil/cm^2.hr.atm$ through the films. The letters $C_o$ through $C_4$ indicate five series of films comprised of the following materials: $C_o$ represents a plurality of films consisting of 100 percent cellulose acetate with acetyl contents ranging from 32 to 45 percent; $C_1$ represents a plurality of films consisting of 85.12 percent cellulose acetate, 12.76 percent polyethylene glycol having a molecular weight of 400 and 2.12 percent polyoxypropylene glycol having a molecular weight of 950; $C_2$ represents films consisting of 76.60% cellulose acetate, the same amount of polyethylene glycol and polyoxypropylene glycol of $C_1$, and 8.52% hydroxybutyl methylcellulose; $C_3$ represents films consisting of 68.10 percent cellulose acetate, the same amount of polyethylene glycol and polyoxypropylene glycol of $C_1$, and 17.02% hydroxybutyl methylcellulose; and $C_4$ represents films consisting of 59.60% cellulose acetate, the same amount of polyethylene glycol and polyoxypropylene glycol as in $C_1$, and 25.52% of hydroxybutyl methylcellulose.

EXAMPLE 8

A plurality of films were prepared and their $k\pi$ values measured by following the procedures of Examples 1 and 6. The results obtained were recorded in Table 4. In the table, the abbreviations have the following significance: C.A. indicates cellulose acetate; the numbers 32 to 38.3 indicate in percent the acetyl content in the cellulose polymer; $A_o$ indicates the film additionally contains 12.76 percent polyethylene glycol having a molecular weight of 400 and 2.12 percent polyoxypropylene glycol having a molecular weight of 950; $A_1$ indicates the film additionally contains the same amount of the polyethylene glycol and polyoxypropylene glycol of $A_o$ and it also contains 8.5 percent hydroxybutyl methylcellulose; $A_2$ indicates the film additionally contains the same amount of the polyethylene glycol and polyoxypropylene glycol of $A_o$ and it also contains 17.02% hydroxybutyl methylcellulose; $A_3$ indicates the film contains the polyethylene glycol and polyoxypropylene glycol of $A_o$ and it also contains 25.52% hydroxybutyl methylcellulose; $K_2SO_4$ is potassium sulfate; KCl is potassium chloride; T.M. is theophylline monoethanolamine; the osmotic pressure $\pi$ is in atmospheres; $k\pi$ is the volume of water transported per unit time through a film of unit thickness per unit area expressed as $cm^3 \cdot mil/cm^2 \cdot hr$; $k$ is water permeability in $cm^3 \cdot mil/cm^2 \cdot hr \cdot \pi$, obtained by dividing $k\pi$ by $\pi$.

TABLE 4

| Film | Osmotic Attractant | Osmotic Pressure $\pi$ | $k\pi$ | $k$ |
|---|---|---|---|---|
| CA 32 | $K_2SO_4$ | 39 | 0.043 | $1.10 \times 10^{-3}$ |
| CA 32 | KCl | 245 | 0.27 | $1.10 \times 10^{-3}$ |
| CA 32 | T.M. | 55 | 0.06 | $1.09 \times 10^{-3}$ |
| CA 32 + $A_0$ | $K_2SO_4$ | 39 | 0.1 | $2.56 \times 10^{-3}$ |
| CA 32 + $A_1$ | $K_2SO_4$ | 39 | 0.15 | $3.84 \times 10^{-3}$ |
| CA 32 + $A_2$ | $K_2SO_4$ | 39 | 0.2 | $5.12 \times 10^{-3}$ |
| CA 32 + $A_3$ | $K_2SO_4$ | 39 | 0.25 | $6.41 \times 10^{-3}$ |
| CA 34.06 | KCl | 245 | 0.165 | $6.73 \times 10^{-4}$ |
| CA 34.06 | T.M. | 55 | 0.037 | $6.72 \times 10^{-4}$ |
| CA 34.06 + $A_0$ | T.M. | 55 | 0.085 | $1.50 \times 10^{-3}$ |
| CA 34.06 + $A_1$ | T.M. | 55 | 0.13 | $2.30 \times 10^{-3}$ |
| CA 34.06 + $A_2$ | T.M. | 55 | 0.18 | $3.27 \times 10^{-3}$ |
| CA 34.06 + $A_3$ | T.M. | 55 | 0.215 | $3.90 \times 10^{-3}$ |
| CA 35 | T.M. | 55 | 0.03 | $5.45 \times 10^{-4}$ |
| CA 35 | KCl | 245 | 0.125 | $5.10 \times 10^{-4}$ |
| CA 35 + $A_0$ | T.M. | 55 | 0.07 | $1.27 \times 10^{-3}$ |
| CA 35 + $A_1$ | T.M. | 55 | 0.1 | $1.80 \times 10^{-3}$ |
| CA 35 + $A_2$ | T.M. | 55 | 0.14 | $2.50 \times 10^{-3}$ |
| CA 35 + $A_3$ | T.M. | 55 | 0.17 | $3.10 \times 10^{-3}$ |
| CA 38 | KCl | 245 | 0.053 | $2.16 \times 10^{-4}$ |
| CA 38.3 + $A_0$ | KCl | 245 | 0.13 | $5.30 \times 10^{-4}$ |
| Ca 38.3 + $A_1$ | KCl | 245 | 0.19 | $7.70 \times 10^{-4}$ |
| CA 38.3 + $A_2$ | KCl | 245 | 0.26 | $1.06 \times 10^{-3}$ |
| CA 38.3 + $A_3$ | KCl | 245 | 0.32 | $1.31 \times 10^{-3}$ |

EXAMPLE 9

An osmotic therapeutic system for the controlled and continuous oral release of the beneficial agent sodium acetazolamide was made as follows: to 138 grams of wall forming cellulose acetate having an acetyl content of 32% was added 73.6 grams of the stabilizer cellulose acetate having an acetyl content of 39.8%, 18.4 grams of the flux enhancer polyethylene glycol of the formula $H-OCH_2CH_2-OH$ wherein $n$ is 8.2 to 9.1 and 5520 grams of solvent consisting of acetone:water in the ratio of 88.5:11.5 and the materials blended in a commercially available high shear blender. The materials were blended at room temperature and atmospheric pressure for 30 minutes to produce a homogenous blend that had a solid content of 4%.

Next, 170 grams of sodium acetazolamide and 8.5 grams of the binder 5% (polyvinylpyrrolidone) in isopropyl alcohol were blended in a standard v-blender for 45 minutes to produce wet granules. The granules were dried in an oven at 50° C for 48 hours and passed through a standard No. 30 mesh sieve. Then, 1.8 grams of the lubricant magnesium stearate were separately passed through the No. 30 sieve and the former granules mixed with the latter in the blender for about 30 minutes, or until a uniform mixture was obtained. The mixture was then compressed in a conventional Manesty tableting machine using a 5/16 inch diameter concave punch to produce compressed tablets having a hardness of about 9 kg as measured by a Strong-Cobb hardness tester.

Next, the above prepared wall forming composite and the tablets were placed in a Wurster air suspension machine and the tablets air tumbled until they were uniformly coated. The tablets were dried in an oven at 50° C for one week to yield a final coat 5 mils thick weighing 21 mgs on each tablet. Finally, a 5 mil aperture was mechanically drilled through the composite wall to produce the osmotic device with each containing 170 mg of sodium acetazolamide, 8.5 mg of polyvinylpyrrolidone and 1.81 mg of magnesium stearate. The in vitro release rate for the devices was measured in a release rate machine that consisted of a series of test tubes with each tube containing 25 ml of distilled water at 37° C. The test was carried out by placing the devices in the first tubes for one hour, then the devices were transferred to the second tubes for one hour, and then with matching places into the remaining tubes. The devices were slowly oscillated throughout the test in the tubes. The amount of acetazolamide released was measured spectrophotometrically at 265 m$\mu$ at low pH. The device had a controlled and continuous rate of release of about 18 mgs per hour over a prolonged period of 6 hours.

EXAMPLE 10

The procedure of Example 9 was repeated in this example with all conditions as described except that the wall of the device was formed essentially free of the stabilizer added in Example 9 to impart inertness to the wall in the presence of sodium acetazolamide. The composition used to form the wall in this example consists of 218.5 grams of cellulose acetate having an acetyl content of 32% and 11.5 grams of polyethylene glycol having a molecular weight of 400 dissolved in 5520 grams of the solvent methylene chloride:methanol mixed in the ratio of 80:20. The amount of sodium acetazolamide released was measured as previously described and the device had an increasing rate of release from 10 to 35 mgs over up to three hours and a decreasing rate of release from 35 to 8 mg from three hours up to six hours of release time.

EXAMPLE 11

A plurality of osmotic drug delivery devices are manufactured according to the procedure of Example 9 wherein the conditions were as described except that the drug of Example 9 was replaced by an orally administrable drug selected from the group consisting of methazolamide, ethoxyolamide, diazepam, amitriptylene hydrochloride, imipramine hydrochloride, naicin, benzthiazide, chlorothiazide, tolbutamide, tolazamide, chloropropamide, procainamide hydrochloride, colchicine, and atropine.

EXAMPLE 12

An oral osmotic device for releasing the vitamin ascorbic acid in the gastrointestinal tract was manufactured as follows: first, a wall forming composition was prepared by thoroughly blending in a high shear blender for 45 minutes at 22.2° C and 1 atmosphere a batch consisting of 61% cellulose acetate having an acetyl content of 32%, 29% cellulose acetate having an acetyl content of 38.3% and 10% polyethylene glycol having a molecular weight of 400 dissolved in acetone:- water solvent formulated on a 90:10 weight-by-weight ratio to produce a homogenous composite.

Next, 200 grams of ascorbic acid was slowly added to 10 grams of ethylcellulose in 100 milliliters of isopropyl alcohol and the materials blended for 45 minutes to produce wet granules. The granules were dried at 50° C for 48 hours and then passed through a No. 20 mesh sieve. Then, the granules were lubricated with 1% magnesium stearate by mixing in a blender and after 30 minutes of blending they were passed through a No. 20 sieve. The granules were then pressed into a solid mass using a standard tableting machine and a 14.8 mm diameter punch. The compressed mass had a finished hardness of 7 kg as measured by a Strong-Cobb hardness tester.

Next, the compressed mass and the wall forming composite were placed in a Wurster air suspension machine and the mass coated until each had a coat 4.7 mils thick. An osmotic passageway 7 mils thick was drilled through the wall to yield the osmotic device. Each device contained 400 mgs of ascorbic acid and had a continuous release rate of about 30 mgs per hour over a period of 8 hours.

EXAMPLE 13

The procedure of Example 12 is repeated but ascorbic acid is replaced by nicotinamide, mannitol hexanitrate, isocarboxyazid, triamcinolone, tranylcypromine, meprobramate, malamide, salicylamide, or aspirin to give the corresponding osmotic device.

EXAMPLES 14 – 15

Two oral osmotic devices were manufactured following the procedure of Example 9. The wall of each device consisted of a composite of 40% cellulose acetate having a 32% acetyl content, 40% cellulose acetate having an acetyl content of 38.3% and 20% polyethylene glycol having a molecular weight of 400. The compartment of one device contained 317 mg of aminophylline compounded with ethylenediamine having the equivalent of 250 mg of theophylline, 15.85 mg of poly(vinylpyrollidone) and 3.17 mg of magnesium stearate. The wall of this device was 7.5 mils thick and the device had a rate of release of about 18 mgs per hour through an osmotic passageway having a diameter of 7 mils. The compartment of the other device contained 333.3 mg of theophylline monoethanolamine having an equivalency of 250 mg of theophylline, 16.67 mg of poly(vinylpyrrolidone), 9.5 mg of pharmaceutically acceptable red No. 3 aluminum lake and 3.17 mg of magnesium stearate. The wall of this device was 7.5 mils thick and the device had a release rate of 22 mg per hour through an osmotic passageway having a diameter of 7 mils.

EXAMPLE 16

An osmotic device for releasing theophylline monoethanolamine over a six hour period was manufactured using the above described procedures. The wall of the device consisted of a composite of 22% hydroxybutyl methylcellulose, 43% cellulose acetate having a 32% acetyl content, 21% cellulose acetate having a 38.3% acetyl content, 12% polyethylene glycol having a molecular weight of 400 and 2% of polyoxypropylene glycol having a molecular weight of 950. The wall of the device was 5.7 mils thick, the osmotic port had a diameter of 10 mils, the compartment contained 125 mgs of theophylline present as monoethanolamine, and the device had a rate of release of 19 mgs per hour.

EXAMPLE 17

An osmotic device for releasing potassium chloride for a prolonged period of 12 hours was manufactured using the above described procedures and apparatus. The wall of the device comprised a composite of 26% hydroxybutyl methylcellulose, 59% cellulose acetate having a 38.3% acetyl content, 13% polyethylene glycol having a molecular weight of 400 and 2% polyoxypropylene glycol having a molecular weight of 950. The wall of the device was 6 mils thick, the osmotic port had a diameter of 10 mils and the compartment contained 750 mgs of potassium chloride.

The release rate for the device was measured in a bath that consisted of a series of 12 tubes with each tube containing 25 ml of double distilled water at 37.5° C. The test was carried out by placing the device in the first tube for one hour, then the device was transferred to the second tube for one hour, and then with matching places into the remaining tubes. The devices were slowly oscillated throughout the test in the tubes containing the test solution. The amount of potassium chloride delivered was determined by electrical conductive measurements for each tube using a conductivity meter calibrated with known standards. The measured rate of release was about 55 mgs of potassium chloride per hour over a prolonged period of 12 hours.

The novel osmotic devices of this invention use means for the obtainment of precise release rates in the environment of use while simultaneously maintaining the integrity of the device. While there has been described and pointed out features of the invention as applied to presently preferred embodiments, those skilled in the art will appreciate that various modifications, changes, additions and omissions in the devices illustrated and described can be made without departing from the spirit of the invention.

What is claimed is:

1. An osmotic device for dispensing a drug to an animal comprising:

(a) a shaped wall that is substantially inert and maintains its physical and chemical integrity during the controlled dispensing of the drug comprising: (1) a semipermeable wall forming material that is permeable to the passage of an external fluid and substantially impermeable to the passage of the drug, said semipermeable material being a polymer of the following formula

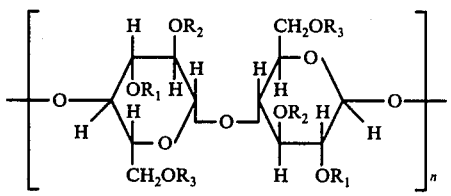

wherein $R_1$, $R_2$, and $R_3$ are selected from the group consisting of hydrogen, alkyl, alkenyl, and acyl and $n$ is greater than 5, and (2) a stabilizing material that imparts inertness and stability to the wall, and which stabilizing material is a different polymer of the following formula:

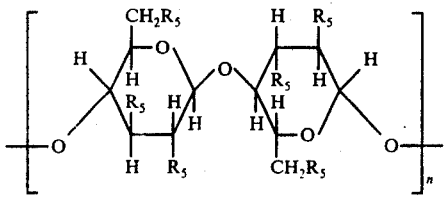

wherein $R_5$ is a member selected from the group consisting of hydroxyl, alkoxy, hydroxyl-substituted alkoxy, alkylcarbonate, alkylcarbamate, alkylsulfonate, alkylsulfamate, and acyloxy, and $n$ is greater than 5;

(b) a compartment formed by the shaped wall and containing the drug, said drug being a member selected from the group consisting of locally and systemically acting drugs;

(c) a passageway in the wall communicating with the compartment and the exterior of the device for dispensing the drug from the device; and, (d) wherein in operation when the device is dispensing the drug to the animal, fluid therefrom is continuously imbibed through the wall into the compartment in a tendency towards osmotic equilibrium at a rate determined by the permeability of the wall and the osmotic pressure gradient across the wall, thereby forming a solution containing drug which is dispensed through the passageway at a controlled rate, with the wall substantially maintaining its inertness and integrity in the presence of the drug and solution thereof over a prolonged period of time.

2. The osmotic device for dispensing a drug according to claim 1, wherein the device is sized, shaped and adapted as a dosage form for the administration of locally and systemically acting drugs to the gastro-intestinal tract and the semipermeable wall forming polymeric material has a degree of substitution on its anhydroglucose groups greater than 0 and up to 3 inclusive.

3. The osmotic device for dispensing a drug according to claim 1, wherein at least one of $R_1$, $R_2$ and $R_3$ is acyl and the semipermeable wall forming material is a member selected from the group consisting of cellulose acetate, cellulose diacetate, cellulose triacetate, cellulose propionate, cellulose acetate propionate, and cellulose acetate butyrate.

4. The osmotic device for dispensing a drug according to claim 1, wherein the stabilizer material has a degree of substitution on its anhydroglucose groups of greater than 0 and up to 3 inclusive, and is a different material than the semipermeable wall forming material and which stabilizer material is a member selected from the group consisting of cellulose esters, cellulose ethers, mixed cellulose esters and ethers, cellulose acetate, cellulose diacetate, cellulose triacetate, hydroxyethyl methylcellulose, hydroxypropyl methylcellulose, hydroxyethyl cellulose, hydroxypropyl cellulose, hydroxybutyl cellulose, and hydroxybutyl methyl methylcellulose.

5. The osmotic device for dispensing a drug according to claim 1, wherein the composite wall contains a dispersant that blends the semipermeable and stabilizing materials into the stable wall, said dispersant being a member selected from the group consisting of an amphipathic, anionic, cationic, nonionic and amphoteric dispersants selected from the group consisting of polyoxyalkylene glycols, esters of polyoxyalkylene glycols, esters of polyhydric alcohols, sulfates esters, sulfated amides, quaternary ammonium salts, alkanolamine fatty acids and tertiary alkyl-ammonium salts.

6. The osmotic device for dispensing a drug according to claim 1, wherein the shaped wall contains a plasticizer that lowers the temperature of the second-order transition of the wall, is compatible with the materials forming the wall, increases the flexibility of the wall, and is non-toxic to animals.

7. The osmotic device for dispensing a drug according to claim 1, wherein the shaped wall contains a plasticizer that lowers the temperature of the second-order transition of the wall, is compatible with the materials forming the wall, increases the flexibility of the wall, is non-toxic to animals, and is a member selected from the group consisting of phthalates, phosphates, citrates, adipates, tartrates, sebacates, succinates, glycolates, glycerolates, benzoates, myristates, sulfonamides, and halogenated phenyls.

8. The osmotic device for dispensing a drug according to claim 1, wherein the shaped wall has a permeability to the external fluid of $10^{-5}$ to $10^{-1}$ cc mil/cm$^2$.hr.atm, and it contains a flux enhancer that assists in regulating the permeability of the wall to the passage of external fluid, said flux enhancer being a polyhydric alcohol.

9. The osmotic device for dispensing a drug according to claim 1, wherein the shaped wall has a permeability to the external fluid of $10^{-5}$ to $10^{-1}$ cc.mil/cm$^2$.hr.atm, and it contains a flux enhancer that assists in regulating the permeability of the wall to the passage of external fluid, said flux enhancer being a member selected from the group consisting of aliphatic diols, polyalkylene glycols, poly($\alpha,\omega$)-alkylenediols, esters of, and mixtures thereof.

10. The osmotic device for dispensing drug according to claim 5, wherein the shaped wall contains from 0.001 to 50 parts of a flux enhancer that assists in regulating the fluid permeability of the wall and which flux enhancer is a member selected from the group consisting of hydrophilic and hydrophobic polyalkylene glycols, poly($\alpha,\omega$)-alkylenediols, aliphatic diols and alkylene glycol esters.

11. The osmotic device for dispensing a drug according to claim 5, wherein the shaped wall contains from 0.001 to 50 parts of a flux enhancer that assists in regulating the fluid permeability of the wall and which flux enhancer is an alkylene glycol.

* * * * *